United States Patent
Valerio et al.

(10) Patent No.: US 6,338,728 B1
(45) Date of Patent: *Jan. 15, 2002

(54) CHEST DRAINAGE DEVICE HAVING MULTIPLE OPERATION INDICATORS

(75) Inventors: Michael A. Valerio, Wrentham; Trinh Phung, Attleboro, both of MA (US); Anthony R. Carlone, Bristol, RI (US); Victor E. Santos, Brockton; Lawrence F. Travers, Westport, both of MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/571,570

(22) Filed: May 17, 2000

Related U.S. Application Data

(62) Division of application No. 09/406,996, filed on Sep. 28, 1999, which is a division of application No. 08/783,177, filed on Jan. 14, 1997, now Pat. No. 5,989,234.

(51) Int. Cl.[7] .................................................. A61M 1/00
(52) U.S. Cl. ....................... 604/317; 604/320; 604/323; 604/327; 604/328
(58) Field of Search ................................ 604/317, 318, 604/319, 320, 321, 322, 323, 324, 325, 326, 327, 328; 600/573, 575, 578, 579

(56) References Cited

U.S. PATENT DOCUMENTS

| | | | | |
|---|---|---|---|---|
| 4,747,843 A | * | 5/1988 | Felix et al. | 604/318 |
| 5,507,734 A | * | 4/1996 | Everett, Jr. et al. | 604/320 |
| 5,807,358 A | | 9/1998 | Herweck et al. | |
| 5,989,234 A | * | 11/1999 | Valerio et al. | 604/321 |

OTHER PUBLICATIONS

Code Number A–6000—Pleur–Evac, Adult–Pediatric Single Use Chest Drainage Unit Dry Suction Control Autotransfusion Compatible With Code Number A–1500, Instructions For Use, Deknatel, Inc., Stock P/N: 131119, Issue Date Apr./97.

(List continued on next page.)

*Primary Examiner*—John G. Weiss
*Assistant Examiner*—Michele Kidwell
(74) *Attorney, Agent, or Firm*—Richard D. Allison; Thomas J. DesRosier

(57) ABSTRACT

Featured is a device for draining fluids and/or gas from body cavities, including at least a pressure control chamber and a collection chamber being fluidly coupled by a one-way valve thereby establishing a waterless seal between the collection chamber, including the patient, and the suction source. The pressure control chamber also includes a waterless suction pressure control regulator that controls and maintains the suction pressure at or about a selected value. Preferably, the regulator includes a spring operated valve. The device also includes a vent path arrangement having an intermediate chamber and at least two passages that are perpendicular to two adjacent surfaces within the intermediate chamber. The two passages and intermediate chamber are arranged so liquid in the collection chamber does not flow and contaminate the upstream portions of the device when the device is resting on its front side or backside. Also featured is an autotransfusion system including a drainage device and a bag assembly attached thereto. The device and bag assembly are fluidly coupled so the differential pressure established by the device causes the blood from the patient to drain into the bag assembly. In an alternate embodiment, the drainage device is configured to continuously collect and filter a patient's blood and continuously output it for re-infusion back into the patient.

43 Claims, 12 Drawing Sheets

OTHER PUBLICATIONS

Code Number A–6002—Pleur–Evac, Adult/Pediatric Dual Collection Chest Drainage System Dry Suction Control With Autotransfusion Option Compatible With Code Number A–1500, Instructions For Use, Deknatel, Inc., Part No. 115322, Date Issued: Feb./94.

Code Number 0077000—Deknatel, Thora–Klex, Chest Drainage System 2500ML Collection Unit, Instructions For Use, P/N 123581, Issue Date: Oct./96.

Code Number 0077020—Deknatel, Thora–Klex, Chest Drainage System 4000ML Dual Collection, Instructions For Use, P/N 123583, Issued Date: Oct./96.

Code Number 0077030—Deknatel, Thora–Klex, Chest Drainage System 350 ML Collection Unit, Instructions For Use, P/N 123586, Issued Date: Oct./96.

* cited by examiner

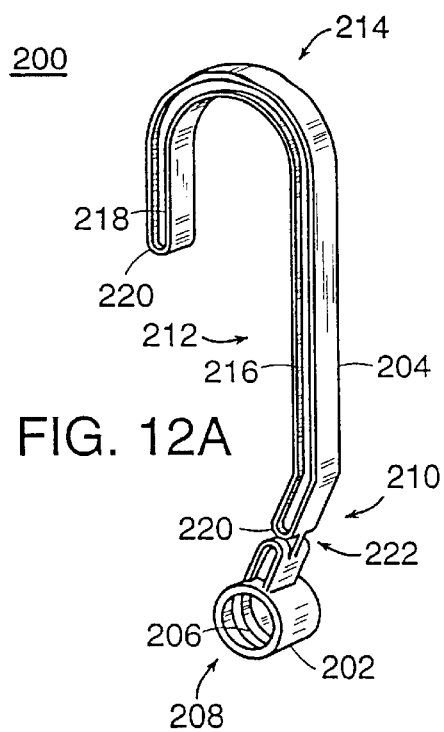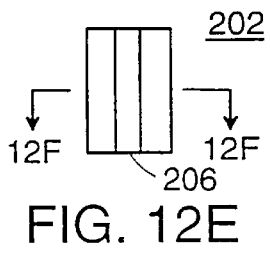
FIG. 12E
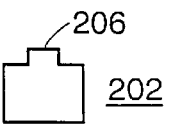
FIG. 12F
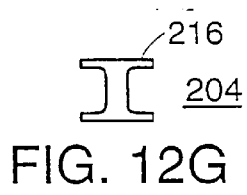
FIG. 12G
FIG. 12A
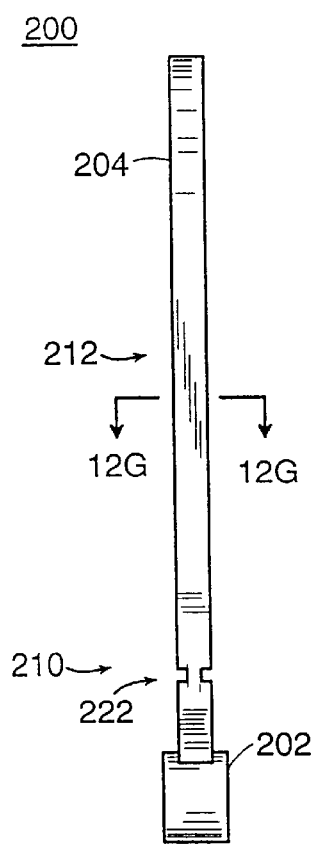
FIG. 12C
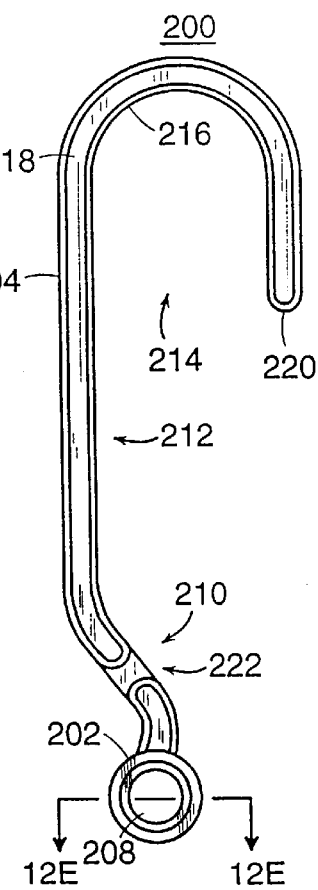
FIG. 12B
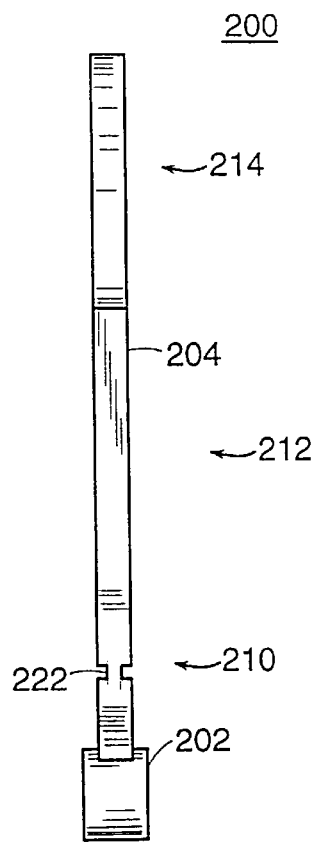
FIG. 12D

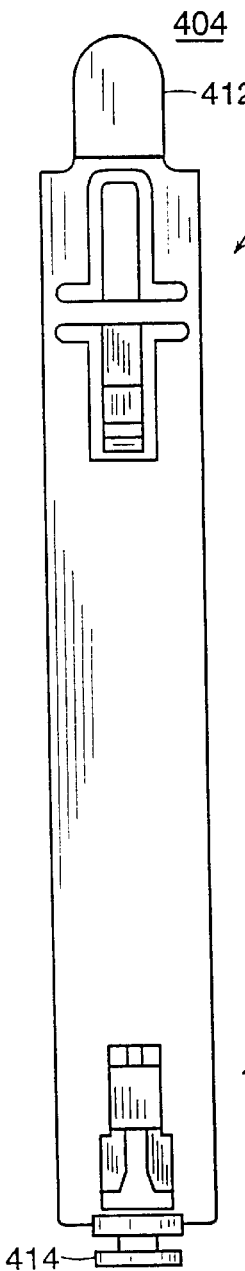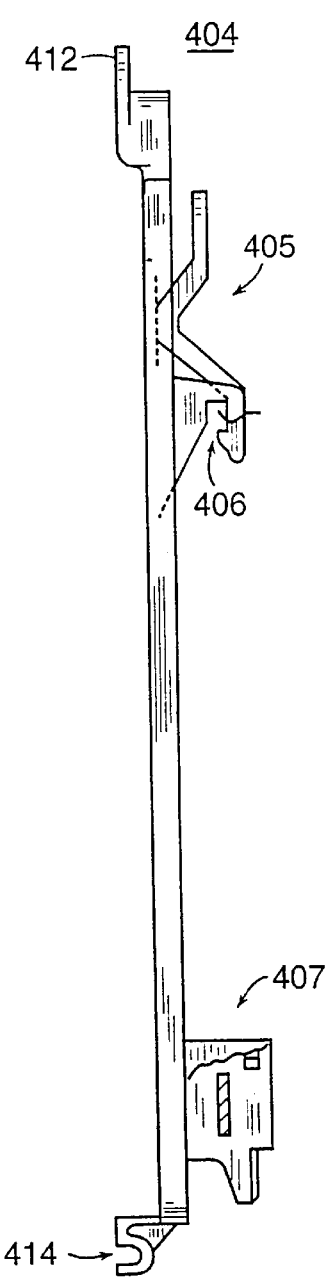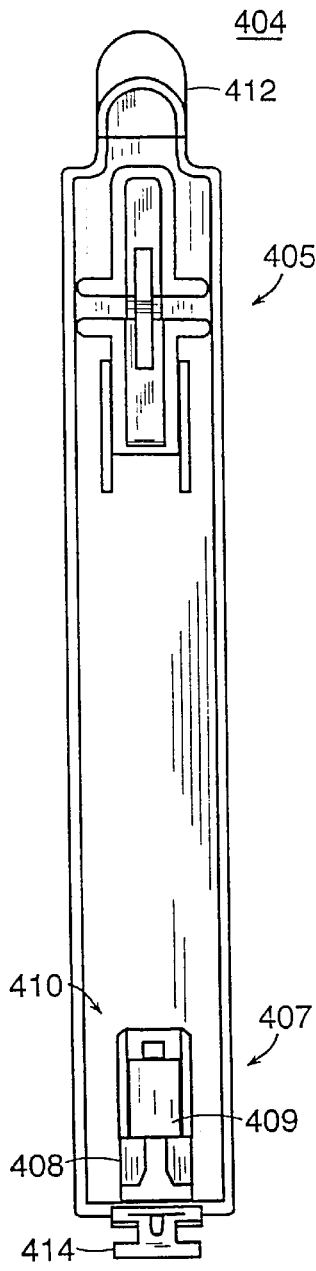
FIG. 15A  FIG. 15B  FIG. 15C
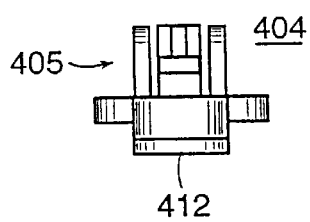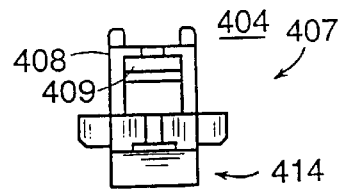
FIG. 15D  FIG. 15E

CHEST DRAINAGE DEVICE HAVING MULTIPLE OPERATION INDICATORS

This is a division of U.S. Ser. No. 09/406,996 filed on Sep. 28, 1999 and which is a division of the earliest patent application U.S. Ser. No. 08/783,177 filed on Jan. 14, 1997, now U.S. Pat. No. 5,989,234.

FIELD OF INVENTION

The present invention relates to drainage devices and systems and more particularly to suction drainage systems and devices for removing gases and/or liquids from medical patients, such as from the pleural cavity, by means of a pressure differential.

BACKGROUND OF THE INVENTION

For many years, the standard apparatus for performing the evacuation of the pleural cavity was a drainage system known as the "3-bottle set-up" which includes a collection bottle, a water seal bottle and a suction control bottle. A catheter runs from the patient's pleural cavity to the collection bottle, and the suction bottle is connected by a tube to a suction source. The three bottles are connected in series by various tubes to apply suction to the pleural cavity to withdraw fluid and air and thereafter discharge the same into the collection bottle. Gases entering the collection bottle bubble through water in the water seal bottle. The water in the water seal also usually prevents the back flow of air into the chest cavity.

Suction pressure is usually provided by a central vacuum supply in a hospital so as to permit withdrawal of fluids such as blood, water and gas from a patient's pleural cavity by establishing a pressure differential between the suction source and the internal pressure in the patient. Such suction pressure (vacuum) and pressure differentials must be precisely maintained because of the dangerous conditions which could result if unduly high or low pressure differentials should occur. However, the hospital suction source typically can vary over time which degrades the suction performance. Also, drainage systems incorporating manometers in the suction control chamber are inconvenient because of the need to add water prior to use, as well as because of their size and weight. In addition, evaporation in the suction control chamber results in suction pressure variations which must be corrected by the addition of more water thereby increasing the maintenance and monitoring time required in the use of such drainage systems.

Also various inefficiencies have existed in the 3-bottle set-up resulting from the many separate components and the large number (usually 16 or 17) of connections. Complications such as pneumothorax may result from the loss of the water seal in the water seal bottle if suction were temporarily disconnected, and undue build-ups of positive pressure could cause tension pneumothorax and possible mediastinal shift. Another serious shortcoming of the 3-bottle set-up is the possibility of incorrect connection and the time necessary to set the system up to monitor its operation.

The 3-bottle set-up lost favor with the introduction of an underwater seal drainage system sold under the name "Pleur-evac"® in 1966 by Deknatel Inc. U.S. Pat. Nos. 3,363,626; 3,363,627; 3,559,647; 3,683,913; 3,782,497; 4,258,824; and U.S. Pat. No. Re. 29,877 are directed to various aspects of the Pleur-evac® system which over the years has provided improvements that eliminated various shortcomings of the 3-bottle set-up. These improvements have included the elimination of variations in the 3-bottle set-up that existed between different manufacturers, hospitals and hospital laboratories. A more detailed description of the need for and the proper use of chest drainage devices is presented in the Deknatel Inc. Pleur-evac® publication entitled "Physiology of the Chest and Thoracic Catheters; Chest Drainage Systems No. 1 of a series from Deknatel" (1985) which is incorporated herein by reference.

Among the features of the Pleur-evac® system which provide its improved performance is a single, pre-formed, self-contained unit that embodies the 3-bottle techniques. The desired values of suction are generally established by the levels of water in the suction control chamber. These levels are filled according to specified values prior to the application of the system to the patient. A special valve referred to as the "High Negativity Valve" is included which is employed when the patient's negativity becomes sufficient to threaten loss of the water seal. Also, a "Positive Pressure Release Valve" in the large arm of the water seal chamber works to prevent a tension pneumothorax when pressure in the large arm of the water seal exceeds a prescribed value because of suction malfunction, accidental clamping or occlusion of the suction tube. The Pleur-evac® system is disposable and helps in the battle to control cross-contamination.

Despite the advantages of the Pleur-evac® system over the 3-bottle set-up and the general acceptance of the device in the medical community, there remains a continuing need to improve the convenience and performance of chest drainage systems and to render such systems compact. As noted above, fluid filled suction control chambers are filled to levels specified by the physician prior to being connected to the patient and the hospital suction system. The levels of suction obtained by such a chest drainage system are somewhat limited by the size (e.g. height) of the chamber required to maintain such suction levels. For high levels of suction, the chamber height required would in some circumstances render the drainage system impractical. In addition, accuracy of such underwater drainage systems is limited in that the fluid chamber employed therein must be constantly monitored visually by observing the liquid level in the respective chambers. Even when gauges are used, they likewise must be constantly monitored. In either case, when the fluid in the chambers evaporates, suction variations can occur which require the addition of more water to compensate for the water loss. All such activity of course is time consuming and is labor intensive.

Because of the size of such devices, they usually present an obstruction between the patient and visitors and the medical staff. As such, it is not uncommon for the device to be knocked over thereby creating the potential for cross-contamination of fluids within the device. These devices, may include some mechanism to minimize cross-contamination if the device falls over on its back, however, there is no protection available if the device falls on its frontside. It is also possible for these units, when knocked over, to become damaged or broken. Because these devices are usually close to the floor when patients are being transported, e.g. between floors of a hospital, it is not uncommon to see a device get broken because they collided with floors, obstructions or when getting on/off elevators.

As a result, the medical staff must take extra care when using such devices so the devices are not inadvertently knocked over or damaged during transportation. If a device is damaged, the medical staff must stabilize the patient, replace the device and clean up the collected fluids that have spilled. This can become even more problematic if the device is being used to collect blood in an autotransfusion process. In addition to the medical staff dealing with the unwanted patient anxiety that may occur, dealing with damaged or broken drainage devices is costly, labor intensive and time consuming. The foregoing also applies to devices that have become cross-contaminated because they are typically replaced by the medical staff.

Other drainage systems or devices have been developed since the introduction of the above described underwater systems to address their perceived shortcomings. One type of drainage device since developed, such as that described in U.S. Pat. No. 5,300,050, uses a waterless pressure regulator as a means for controlling suction pressure and a water filled chamber to establish a seal, the patient seal, between the fluid collection chamber and the suction source. These devices, like the above-described underwater drainage systems, can be damaged during transportation of patients, create an obstruction, and can be knocked over. Also, although these devices may include some protection to minimize cross-contamination if knocked over on their backside, there is no protection if they fall forward.

Another type of drainage device, such as that described in U.S. Pat. Nos. 4,738,671, 4,715,856, 4,544,370, 4,747,844, includes a modulation valve to control the suction flow, and correspondingly the suction pressure being developed, and a one way valve that forms the seal between the suction source and the collection chamber (e.g. the patient seal). In these devices the collection chamber is disposed below the mechanisms for regulating the suction flow and pressure, the mechanism for establishing the patient seal, flow meters and the internal drain and suction lines. These units are complex and involve a large number of parts. Also, because of the direct communication between the seal valve and the collection chamber, the seal valve can come into contact with the collected fluid if the device falls over. These devices, like those described, create an obstruction, can be damaged during transportation of patients and can be knocked over.

Yet another type of device as shown in U.S. Pat. No. 4,605,400, uses a plurality of one way valves to control suction pressure and one, or two one-way valves in series, as a one-way seal between the suction source and the collection chamber. The collection chamber is located below the other controlling parts of the device. A trap is provided between the seal valve(s) and the collection chamber to collect any liquids inadvertently withdrawn through the suction line therebetween. However, there is no barrier between the one-way seal and the suction source and other parts of the device. Thus, if the device is knocked over, collected fluid can flow through and contaminate various parts of the device. Moreover, there is the potential for the collected fluid to be drawn into the suction system. As with the above-described devices, this device can be damaged during patient transport and create an obstruction that can lead to the unit being knocked over.

In sum, it is common for prior art devices to get knocked over, which can have adverse consequences, and for them to get damaged during patient transport. This creates an environment where the medical staff must exercise extra care to avoid unwanted consequences. It also creates a labor intensive, time consuming and expensive environment.

Accordingly, there is a need for an improved device or system as well as methods related thereto for removing gases and liquids from medical patients where suction pressure control and the collection chamber seal does not involve the use of liquids. Further, there is a need for an improved mechanism for venting the collection chamber that is more resistant to cross contamination than prior art devices and systems. Additionally, there is a need for improved devices that are compact in size and are resistant to overturning as compared to prior art devices.

SUMMARY OF THE INVENTION

The present invention features a novel device for draining gases and/or liquid from the body cavity of a patient. The drainage of liquid, blood, and/or gas from the body cavity is accomplished by establishing a pressure differential between the device and the body cavity to be drained.

Various aspects or features of the drainage device of the instant invention provide a number of benefits as compared to prior art devices. In particular, these features yield a device that is compact as compared to prior art devices and which is more resistant to being overturned as compared to present art devices. This reduces the likelihood of damaging the device during patient transport as well as making it less cumbersome for the medical staff to use (e.g., minimizes obstruction potential).

These features also minimize or avoid the potential for cross contamination within the device whether it is inadvertently knocked over onto its backside or frontside. Other features provide added security, provide multiple indications of suction pressure being developed in the device, and yield a device hanger that can be easily adjusted to fit a given support arrangement.

In a first aspect, a device according to the present invention includes a novel venting or flow path arrangement interposed between a collection chamber, in which fluid (e.g., blood) is accumulated and a one-way valve forming the patient seal. The flow path is arranged to prevent the fluids accumulating in the collection chamber from being communicated upstream to other parts of the device in the event the device falls onto its face or backside.

In particular embodiments, the venting arrangement includes an intermediate chamber positioned proximate the backside of the device and at least two flow passages. One flow passage fluidly couples the intermediate chamber and the collection chamber and another flow passage fluidly couples the intermediate chamber to the flow path going to the patient seal. In a preferred embodiment, two spaced flow passages fluidly couple the intermediate chambers and the collection chamber. These flow passages are also arranged to be essentially perpendicular to the front surface of the device, in a front-to-back type of relationship.

The intermediate chamber is configured with two compartments that are fluidly coupled by means of a stepped opening therebetween which forms a stepped surface. Each collection chamber flow passage forms an aperture in a surface of one compartment and the flow passage to/from the patient seal vent path forms an aperture in a surface of the other compartments. The surface having the collection chamber flow passage aperture(s) is configured so it is lower than the surface of the other compartment, when the device is on its frontside or face.

An opening is provided in each collection chamber flow passage that is in fluid communication with the collection chamber opening is preferably arranged so it lies above the maximum height of the fluid accumulated in the collection chamber, when the device is on its backside. Correspondingly, the length of each collection chamber flow passage and the height of the step, in the intermediate chamber stepped surface, are established so the high point of the stepped surface lies above the fluid level in the collection chamber when the device is on its frontside or face. In this way, accumulated fluid from the collection chamber is not cross-communicated upstream to other parts of the device, if the device is inadvertently knocked over onto its frontside or backside.

In a second aspect, a device of the present invention includes at least two chambers, a pressure regulation chamber and a collection chamber that are fluidly interconnected by a one-way valve that represents the patient seal. The one-way valve permits flow of gases from the collection chamber to the pressure regulation chamber and blocks flow of gases from the pressure regulation chamber to the collection chamber. The collection chamber also includes a port that is in fluid communication with the region to be drained.

The pressure regulation chamber includes two ports, both disposed upstream of the one-way valve, where one port is fluidly interconnected to a source of negative pressure (i.e., a suction source) and the other port is open to atmosphere. The drainage device further includes a suction pressure control mechanism that selectively adjusts the negative pressure being applied to the collection chamber and maintains the negative pressure being applied at or about the selected value. In particular embodiments, the suction pressure control mechanism includes a suction pressure control valve that is a spring loaded and spring operated valve disposed between the atmospheric and suction source ports. The spring is biased or loaded (e.g., tensioned) to any one of a number of predetermined values, each value being representative of a suction or negative pressure to be applied to the collection chamber. The spring also biases the valve so as to be in a closed position until the suction source pressure exceeds the selected applied suction pressure, at which point the suction pressure control valve opens so as to maintain the applied suction pressure at the selected value.

In a preferred embodiment, the one-way valve fluidly inter-connecting the pressure regulation chamber and the collection chamber, is a high precision flapper-type check valve. Such a check valve opens at relatively low differential pressures and functions completely independent of any fluid present in the collection chamber. In a particular embodiment, the check valve opens at a pressure differential of about 0.5 cm of $H_2O$.

More particularly, the check valve includes a disk shaped resilient valve element mounted along the flow path of the valve to permit the flow in one direction only. The disk is maintained normally in a dish shape, with the dish disk being biased toward and against the valve inlet to normally bias the valve in a closed configuration. The operating characteristics of the valve, such as opening pressure and minimum flow rate, are adjustable by a disk mount. The valve also includes an outlet that minimizes back pressure to enable the valve to be quickly responsive even at low pressure differentials. In this way, a dry pressure seal is established between the pressure regulation chamber, the suction source and the collection chamber, which also permits gases being drained from a medical patient to be vented to the suction source while preventing gases from flowing into the collection chamber and correspondingly into the patient.

The waterless suction pressure control mechanism and the one-way valve cooperate so high differential suction pressures and a patient seal can be established in a highly compact and rugged device. The compactness results in a device less likely to be damaged during patient transport. The compactness of the shape also yields a device less likely to be knocked over or overturned while being used (e.g., when placed on the floor beneath a patient's bed).

In a third aspect, a device of the instant invention further includes an air leak meter chamber fluidly interposed between the one-way valve and the collection chamber. The air leak meter chamber includes a fluid filled cavity and a means, responsive to gases flowing from the collection chamber to the suction source, that provides a relative indication of the flow rate of the flowing gases. In a particular embodiment, the indication means includes a downwardly sloping member having a plurality of spaced holes. The sloping member is in fluid communication with the collection chamber so the gases flowing from the collection chamber also can flow through the holes.

The holes and downwardly sloped member cooperate so the gas flowing through each hole is representative of a relative leakage rate. The sloping member also includes a plurality of vertical partitions that separate each of the spaced holes. The partitions provide a mechanism for clearly identifying the hole(s) gas is flowing through and correspondingly an indication of the relative flow rate. Preferably, the front panel of the device includes a transparent window to view the sloping member and the vertical partitions.

In a fourth aspect, a device of the instant invention includes a negative pressure indicator to sense the negative pressure being developed in the collection chamber. The negative pressure indicator includes a message post or board covered by a flexible membrane. The interior of the flexible membrane is fluidly coupled to the collection chamber so as to be responsive to the pressure changes in the collection chamber. Thus, when a negative pressure is established in the collection chamber, the flexible membrane collapses about the message board or post. When this occurs, the message and/or symbol on the message board becomes visible. A separate indication of collection chamber pressure can identify potential problems not otherwise indicated by a suction pressure indicator.

A fifth aspect of the invention features a novel hanger rotatably secured to the sides of the device so the device can be hung from the side rails of a hospital bed or other support mechanisms or structures (e.g. wheelchair). Each hanger includes a hook shaped attachment member having a flex point about which the hanger attachment member can be bent. The medical staff, e.g. nurse, can make local adjustments, e.g. side-to-side, to the hook shaped attachment member so it can accommodate variations in the support mechanism. An attachment to a support mechanism is not required, however, because the device also is configured to be self-supporting. In addition, the device shape and relative dimensions are established to lower the center of gravity in comparison to prior art drainage devices thereby improving the resistance of the device to overturning.

In a sixth aspect of the instant invention, the device is configured to continuously collect patient blood and reinfuse the collected blood back into the patient. More particularly, the collection chamber is configured to filter blood and collect the filtered blood in a portion of the chamber. Further, the portion of the chamber in which the blood is being collected includes sloping bottom surfaces to create a sump in which a drain port is located. This device is connected to a patient as described below so the blood can be re-infused into the patient.

Also featured is an autotransfusion drainage system using the above described drainage device, an attachment interface member and an external bag having a support structure. The interface member is configured to releasable engage attachments or mounts on the device and the framework of the external bag. Alternatively, the external bag can be configured to releasably engage the device attachments or mounts. The external bag also includes two ports/lines that communicate with he interior of the bag. One of the ports is connected to the drain line from the patient's body cavity and the second port is connected to the drain port of the device. In this way, the fluid discharge from the medical patient is collected in the external bag. The external bag further includes a connection used to interconnect the external bag to an I.V. drip line or an I.V. infusion pump so a patient can be infused with the blood collected in the external bag.

The system further includes a filter medium that is preferably positioned so the blood being drained from the patient is filtered before it is collected in the external bag. Alternatively, the blood is collected and then filtered before it is transfused into the patient. In yet another embodiment, the blood being collected is filtered before collection and before transfusion into the patient. Similarly, the above-described alternate device embodiment, can be configured with a filter medium so the blood is filtered before collection, before transfusion or both.

The instant invention also features methods related to the use of the above described devices and systems including use in post operative environments.

DEFINITIONS

The instant invention is most clearly understood with reference to the following definitions:

Autotransfusion shall be understood to mean the collection and the infusion of the collected patient's blood back into the patient.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIGS. 12A–D are various views of a device hanger according to the instant invention;

FIG. 12E is a cross-section view of the hanger hub taken along the section line in FIG. 12B FIG. 12F is a cross-section view of the hanger hub taken along the section line in FIG. 12E;

FIG. 12G is a cross-section view of the hanger attachment member taken along the section line in FIG. 12C;

FIGS. 15A–E are various views of the interface member of FIGS. 14A,B.

DESCRIPTION OF THE PREFERRED EMBODIMENT

Figure 1:
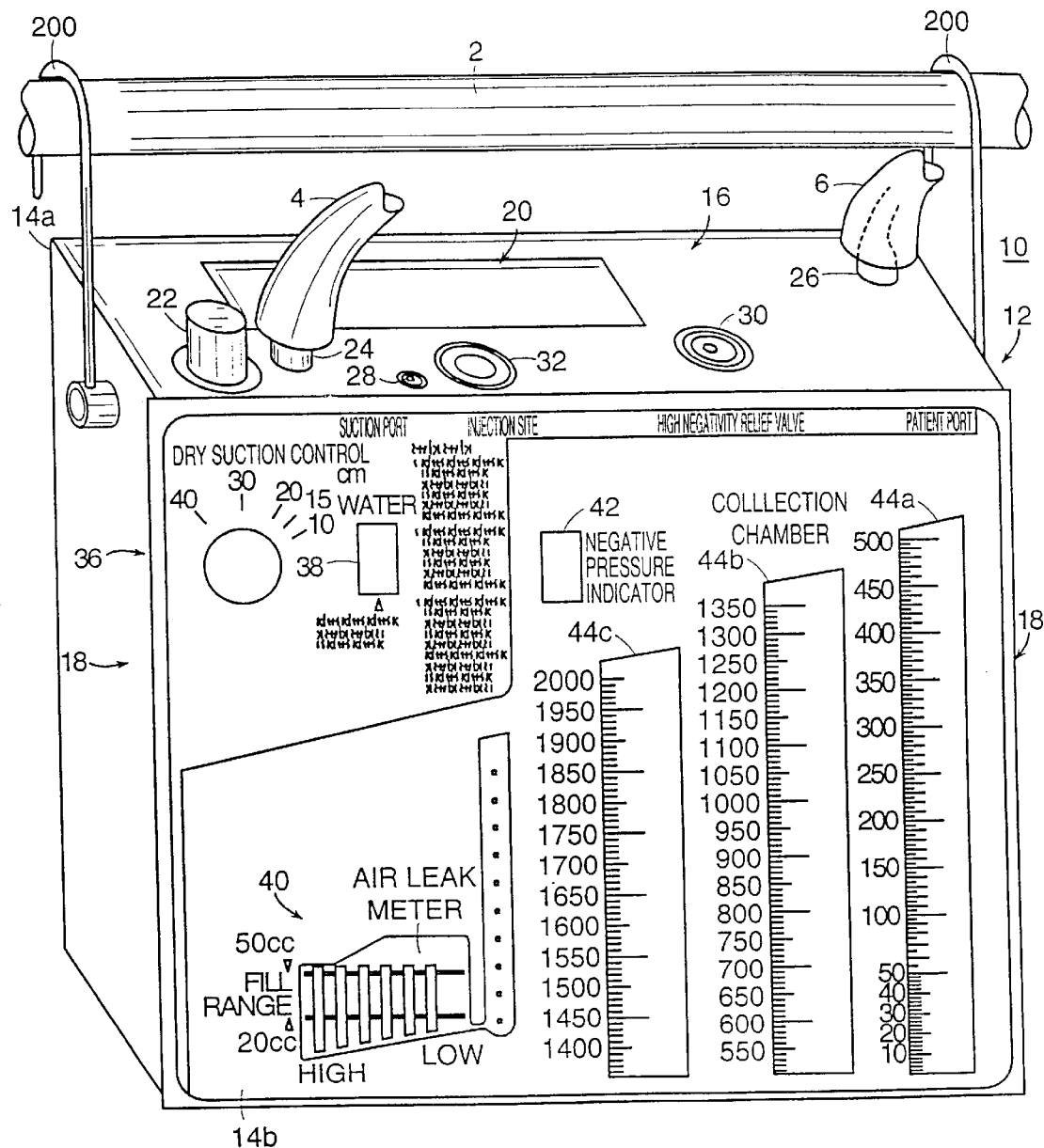
FIG. 1 is an axonometric view of a drainage device of the instant invention.

Referring now to the various figures of the drawing wherein like reference characters refer to like parts, there is shown in FIGS. 1–3 and FIG. 4A a drainage device 10 that can be used to drain gases and liquids from the body cavity of a medical patient (not shown). In one arrangement, the drainage device is hung from a support, such as the side rail 2 of a hospital bed, by means of two hangers 200 rotatably attached to the sides 18 of the device housing 12. The drainage device housing 12 is also formed so the device 10 is self-supporting or self-standing without the need for a means to increase the footprint of the device to improve the device's overturning moment. In an exemplary embodiment, a device 10 according to the instant invention includes a length or width of about 12 in., a depth of about 4 in., and a height of about 10 in. The result is a drainage device 10 that is shorter and less bulky than prior art drainage devices but which can hold about 2 liters (2,000 cc) of liquid.

In use, the drain line 6 from the patient is connected to the patient port 26 of the device 12 housing and the thoracic catheter of the patient. The suction line 4 from the source of negative pressure, the suction source, is connected to the suction port 24. The drain and suction lines 4,6 are medical grade flexible plastic tubing as is known in the art. The suction and patient ports 24,26 typically are about ⅜ in. diameter and are located in the device housing 12 so the suction port is in fluid communication with the suction pressure regulation chamber 46 of the device 10 and so the patient port is in fluid communication with the collection chamber 50.

A high negativity relief valve 30 is disposed in the wall or surface defining the top 16 of the housing 12 and is in fluid communication with the collection chamber 50. The high negativity relief valve 30 includes a button actuated valve which, when depressed, allows filtered air to enter the collection chamber 50. In this way, undesired high degrees of negative pressure that may occur in the body cavity and/or the collection chamber 50 can be relieved. For example, high negativity conditions in the collection chamber 50 can result from stripping or milking of the tubing from the body cavity as well as by the patient in certain circumstances.

In addition to the high negativity relief valve 30, an automatic high negative pressure relief valve 34 is located in the air leak meter chamber 48. The automatic relief valve 34 also is arranged so it is fluidly coupled to atmosphere through the back 17 of the device housing 12. The automatic relief valve 34 is configured to limit the negative pressure to a predetermined value, and in a specific embodiment the set pressure of the valve is about 50 cm of $H_2O$. The automatic relief valve 34 also is configured to allow filtered air to enter the air leak chamber 48 when actuated. In an exemplary embodiment, the automatic relief valve 34 is an adjustable diaphragm check valve as described in U.S. Pat. No. 4,550,749 the teachings of which are incorporated herein by reference.

Also disposed in the housing top 16 is a resealable grommet 32 and a positive pressure relief valve 24. The grommet 32 is provided so the required volume of a liquid, e.g. sterile water solution, can be injected into the air leak meter chamber 32 by the user. The positive relief valve 24 opens with increased positive pressure in the suction pressure regulation chamber 46. For example, coughing by the patient can create momentary high pressure positive conditions in the device.

Preferably, the positive relief valve 24 includes an aperture 52 in the housing top 16, an angled wall 53 having an aperture 54 therethrough, and a ball 55. When negative pressure conditions are established in the suction pressure regulation chamber 46, the ball 55 is drawn into sealing engagement with the wall aperture 54 thereby isolating the suction pressure regulation chamber from atmosphere. However, if a high pressure condition occurs in the suction pressure control chamber 46, the ball 55 is forced out of the sealing engagement and thus does not block the wall aperture 54. In this way, the high pressure air can escape to atmosphere via the aperture 52 in the housing top 16.

The device housing 12 is a unitary housing formed from two portions, a rear or body portion 14a and a front panel 14b. The body portion 14a is molded preferably using a light colored opaque plastic material and is constructed with a number of walls, posts and other like structures which generally extend to the front panel 14b so as to define a plurality of chambers, ribs, compartments and support elements. The front panel 14b is formed from a transparent sheet of plastic material having a substantially uniform thickness. The front panel 14b and body portion are preferably assembled to form the housing 12 by means of linear vibration welding.

As illustrated more clearly in FIG. 1, a graphic mask is printed on the front panel 14b and includes a plurality of windows, status indicators, and calibration or measuring indicia, as well as other information provided for the user. Alternatively, a label or mask may be applied using any of a number of techniques known to those skilled in the art. Among the so-called windows defined by the mask, are a suction status window 38, an air leak meter window 40 and a negative pressure indicator window 42 that are aligned over the corresponding chamber or compartment in the device 10. Also defined are a plurality of windows 44a–c, where a window is aligned with each compartment 116a–c of the collection chamber 50.

In addition to defining windows, the mask also includes opaque regions that cover large regions of the front panel. Preferably selected areas of the opaque regions include the indicia provided for calibration or measuring activities. For example, indicia are provided along with each window 44a–c corresponding to a collection chamber compartment so a user can easily and readily determine the amount of fluid that has been collected (i.e. a running total of the amount of the collected fluid). The indicia provided for the air leak meter window 40 also preferably include a fill line to indicate the appropriate water level for monitoring air leaks. As discussed hereinafter, indicia representative of the desired suction pressure to be applied are provided proximate the dry suction control knob 36.

Figure 3:
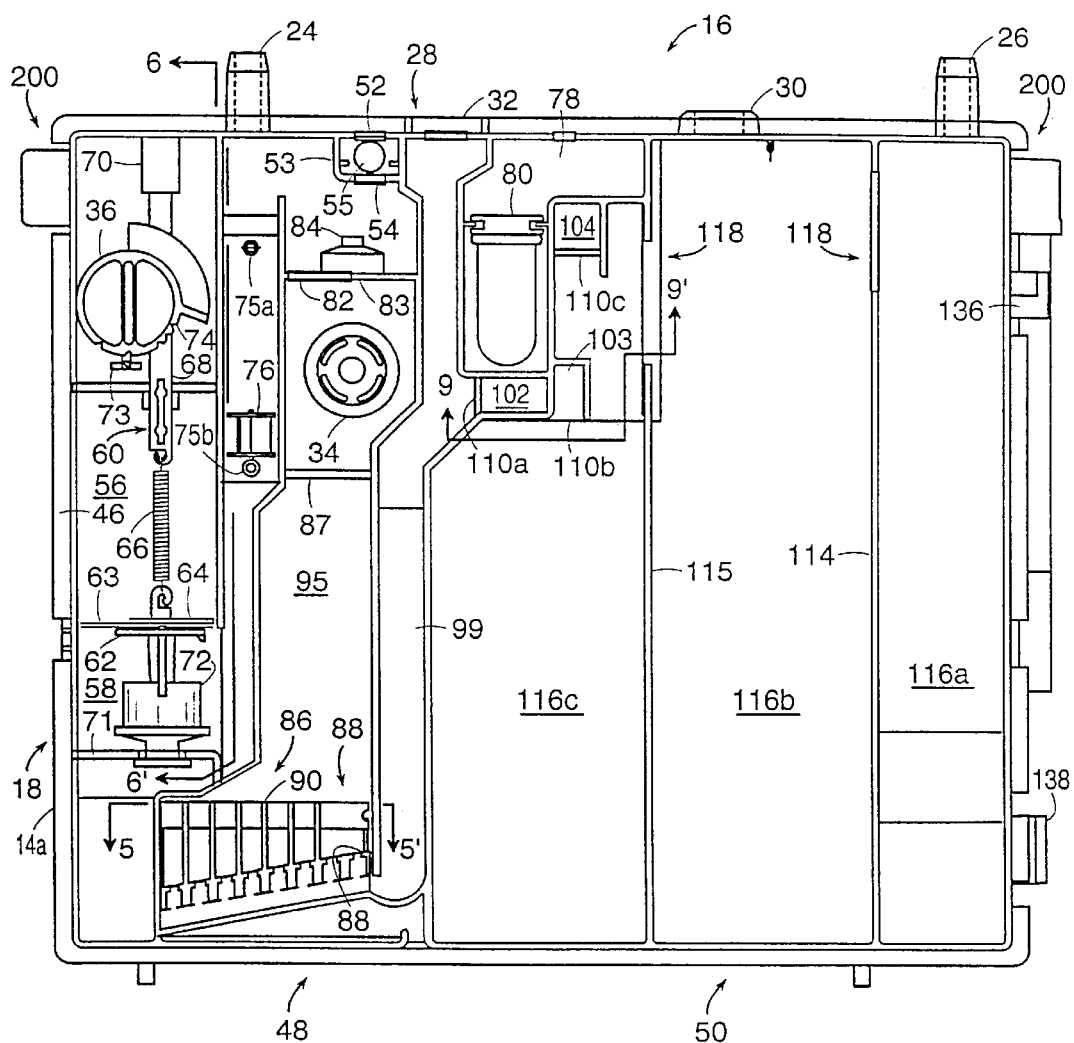
FIG. 3 is a cross-sectional front view of the drainage device taken along section line 3–3' of FIG. 2.
Figure 6:
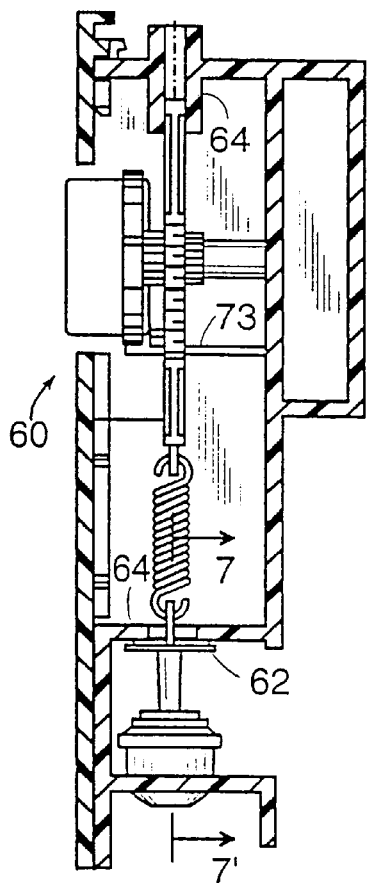
FIG. 6 is section 6–6' of FIG. 3.
Figure 7:
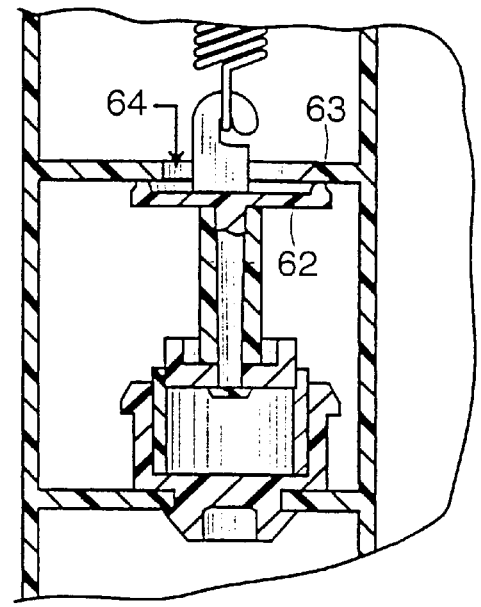
FIG. 7 is section 7–7' of FIG. 6.

As indicated above the walls, ribs and partitions internal to the device housing 12 define three internal chambers; a suction pressure regulation chamber 46, an air leak meter chamber 48 and a collection chamber 50. As shown in FIG. 3 and FIGS. 6–7, the suction pressure regulation chamber 46 includes a number of walls and partitions that define a first compartment 56 and a second compartment 58. The upper end of the first compartment 56 has an opening 22 which communicates with the atmosphere and the second compartment 58 is fluidly coupled to the suction port 24. Disposed in the first and second compartments 56, 58 is a pressure regulator 60, that includes a valve 62. The valve 62 is dimensioned and configured to seat against the opening 64 in a plate member 63 that separates the first and second compartments.

The valve 62 is a plate type of valve that is biased in a closed position by means of a coil spring 66. The coil spring 66 is secured to one end of a rod 68 whose other end is positioned within a rotatable joint annular collar 70 or coupling that is secured to the housing top 16. The annular collar 70 also includes a key way ridge that is received within a groove along the upper end of the rod 68. In this way, the rod 68 can be rotated together with the collar 70 and simultaneously advanced upwardly or downwardly to calibrate the suction regulator 60 as described in more detail in U.S. Pat. No. 5,707,734 the teachings of which are incorporated herein by reference.

The valve 62, as shown more clearly in FIG. 7, is formed on the end of a dashpot 72 that is secured in a slotted opening in the plate member 71 that defines the lower end of the second compartment 58. The dashpot 72 attenuates the rapid modulation of the valve 62 that may occur during operation of the drainage device 10. Preferably, the valve 62 is formed of a material, such as a high density polyethylene, that is more pliable than the plate member 63 separating the two compartments 56,58 so the valve 62 more easily conforms to any irregularities in the plate member 63 and to assure proper sealing of the opening 64.

As more clearly shown in FIG. 6, the rod 68 includes a portion having a worm gear that cooperates with a gear positioned on a shaft that supports the rotatably mounted suction control knob 36. As the knob 36 is rotated, the gear also is rotated so as to cause the rod 68 to advance upwardly or downwardly while the collar 70 remains fixed or non-rotating. In this way, the tension in the spring 66 is changed. Because the tensioning of the spring 66 provides the force to seat the valve 62 against the plate member 63, as hereinabove described, this also changes the seating forces. The tension also corresponds to the suction pressure being applied to the collection chamber 46 and correspondingly the body cavity of the patient to be drained.

A series of detents 74 are provided along specific portions of the circumference of a portion of the control knob 36 that engage a stop arm 73 mounted to the housing 12. The detents 74 correspond to any one of a number of predetermined levels of suction or negative pressure. Thus, in operation a user rotates the knob 36 and engages a detent 74 corresponding to one of the suction levels indicated on the mask applied to the front panel and the tension in the spring 66 is thereby adjusted so the selected suction pressure is developed.

For further details regarding the construction and operation of the pressure regulator 60 of the instant invention reference shall be made to U.S. Pat. Nos. 5,507,734 and 5,300,050, the teachings of which are incorporated herein by reference.

The suction pressure regulation chamber 46 also includes a visual indication to confirm the establishment of a suction pressure condition in the collection chamber. Preferably, the visual indication is supplied by a float member 76 that is slidably disposed in a portion of the second compartment 58. The float member 76 is dimensioned so it moves upwardly against an upper stop member 75a, e.g., a post, when the suction pressure is developed. The float member 76 is visible to the user through the suction pressure indicator window 38 when it is up against the upper stop member 75a. As further assistance to the user, the float member 76 is colored in contrast to its surroundings so as to make it readily visible to the user. In a specific embodiment, the float member 76 is fluorescent to make it easier to see in reduced light or night time conditions. When there is no suction pressure, the float member 76 rests against the lower support member 75b.

Another compartment 78 is provided in the drainage device 10 in which is mounted a negative pressure indicator 80. By means of an aperture 79 in the intermediate chamber 100 (see FIG. 10), the negative pressure indicator 80 is responsive to the pressure conditions in the collection chamber. In this way, the indicator 80 can provide an indication that there is a negative pressure condition within the collection chamber 50. This indication is readily visible to the user in the negative pressure indicator window 42.

In an exemplary embodiment, the pressure indicator 80 is a message post or message board covered with a flexible material. When a negative pressure condition exists in the collection chamber 50, the flexible material, by means of the aperture 79, collapses onto the post and the message or symbol thereon becomes visible. If negative pressure is not present the flexible material moves away from the message post or message board so the message or symbol is not visible.

Referring back to FIG. 3, a plate member 82, having an aperture 83 therein for receiving one end of a one-way valve 84, extends between two plate members. The plate member 82 in conjunction with the one-way valve 84 defines a pressure boundary between the suction pressure regulation chamber 46 and the air leak meter chamber 48 and correspondingly the collection chamber 50. As hereinafter provided, a user may not use the air leak meter chamber 48 and not introduce any water therein. As such, the plate member 82 in conjunction with the one-way valve 84 also defines a pressure boundary between the suction pressure regulation chamber 46 and the collection chamber 50. Accordingly, and in an alternate embodiment, a drainage device 10 can be configured with only a suction pressure regulation chamber 46 and a collection chamber 50.

Preferably, the one-way valve member 84, is a high precision flapper-type or diaphragm check valve as described in U.S. Pat. Nos. 4,715,856, 4,747,844 the teachings of which are incorporated herein by reference. Such a check valve opens at relatively low differential pressures and functions completely independent of any fluid present in the collection chamber 50 and/or in the air leak meter chamber 48. In a particular embodiment, the check valve opens at a pressure differential of about 0.5 cm of H$_2$O.

Figure 8:
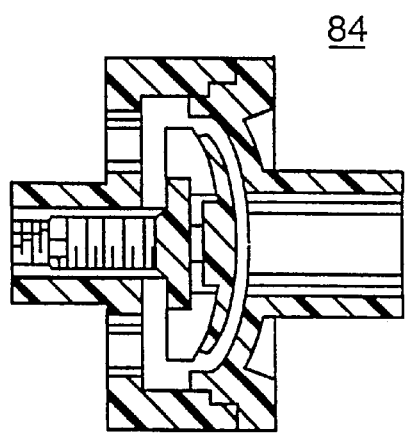
FIG. 8 is a cross-sectional side view of an automatic high pressure negativity relief valve.

More particularly, and as shown in FIG. 8, the check valve or one-way valve 84 includes a disk shaped resilient valve element along the flow path of the valve to permit the flow in one direction only. The disk is maintained normally in a dish shape, with the dish disk being biased toward and against the valve inlet to normally bias the check valve in a closed configuration. The operating characteristics of the check valve, such as opening pressure and minimum flow rate, are adjustable by a disk mount. The check valve also includes an outlet that minimizes back pressure to enable it to be quickly responsive even at low pressure differentials. In this way, a waterless seal is established between the pressure regulation chamber 46, the suction source and the collection chamber 50, which permits gases drawn from a medical patient's body cavity to be vented to the suction source while preventing gas flow into the collection chamber and correspondingly into the patient.

The drainage device 10 of the instant invention does not use a manometer to control suction pressure or to establish a seal between the suction pressure regulation chamber 46 and the collection chamber 50, and correspondingly, the patient. As such, the drainage device 10 of the instant invention is shorter in comparison to prior art devices that use such manometers for suction control or for the patient seal. This advantageously lowers the center of gravity of the drainage device 10 as compared to prior art drainage devices which in turn improves the resistance of the present invention to overturning. Also, by using a waterless suction pressure control, the suction pressure can be maintained without requiring the constant attention of the medical staff.

Referring now to FIG. 3 and FIGS. 5A–D, at the lower end of the air leak meter chamber which is 48 there is provided an enlarged cavity 86 in which is disposed an air leak meter or air flow meter 88. The air flow meter 88 measures the amount of gas or air passing through the collection chamber 50 to the vacuum pump or vacuum source. In normal operational conditions, the air flow meter 88 provides an indication of the amount of air or gas being evacuated from the body cavity, e.g., pleural cavity, of the patient. By monitoring the air flow meter 88, a user or clinician can readily determine if the flow is increasing or decreasing. The air flow meter 88 also provides an indication of the presence of an air leak somewhere between the body cavity and the flow meter which could be hazardous to a patient's condition if left uncorrected. For example, an air leak could create conditions in the pleural cavity that would make breathing difficult for the patient, which could lead to death.

The construction of the air flow meter 88 is shown in greater detail in FIGS. 5A–D and FIG. 5A further illustrates the relationship of the air flow meter with the drainage device 10 of the instant invention. The air flow meter 88 is provided with a rear wall 90 and a front wall 92, which includes a common duct or passageway 94 formed therein. The front wall 92 and the rear wall 90 have an interconnecting portion 91 which forms the upper wall of the passageway. The interconnecting portion 91 includes a series of apertures 96 beneath each of which is formed a plenum chamber 97 that is fluidly coupled to the common passageway 94. Disposed above and separating each of the apertures 96 is a partition member 98. The partition members 98 provide a mechanism for separating the bubbles passing through each of the apertures 96 so the number of apertures through which gas is passing can be readily determined.

The air flow meter 88 is disposed in the enlarged cavity 86 at a slight angle to the horizontal. One end of the common passageway 94 is fluidly coupled to the small arm 99 of the air leak meter chamber 48 which is fluidly coupled to the novel vent path arrangement, described below, that in turn is fluidly coupled to the collection chamber 50. In this way, gases flowing downwardly in the small arm 99 will flow into the common passageway 94 into one or more of the plenum chambers 97 and thence through one or more of the apertures 96. By inclining the common passageway 94, greater volumes of gas will flow through succeeding apertures 96 in sequence. As such, each of the apertures 96 is representative of a given flow of gas. For example, flow through the first aperture would be representative of a gas flow of about 0 to 2 liters per minute and the flow through the last and all apertures would be representative of a gas flow in excess of 28 liters per minute. For further details regarding the air flow meter 88, reference shall be made to U.S. Pat. No. 3,683,913, the teaching of which are incorporated by reference herein.

In use, a liquid is introduced into the air leak meter chamber 48 by injecting it through the resealable grommet 32. Preferably, a dye or coloring agent also is provided in the enlarged cavity 86 so the fluid is readily observable to the user. Thereafter, the user monitors the air leak meter 88 through the air leak meter window 40 in the front panel 14b to determine if there is any gas being passed to the suction source and, if so, the relative flow rate.

Figure 2:
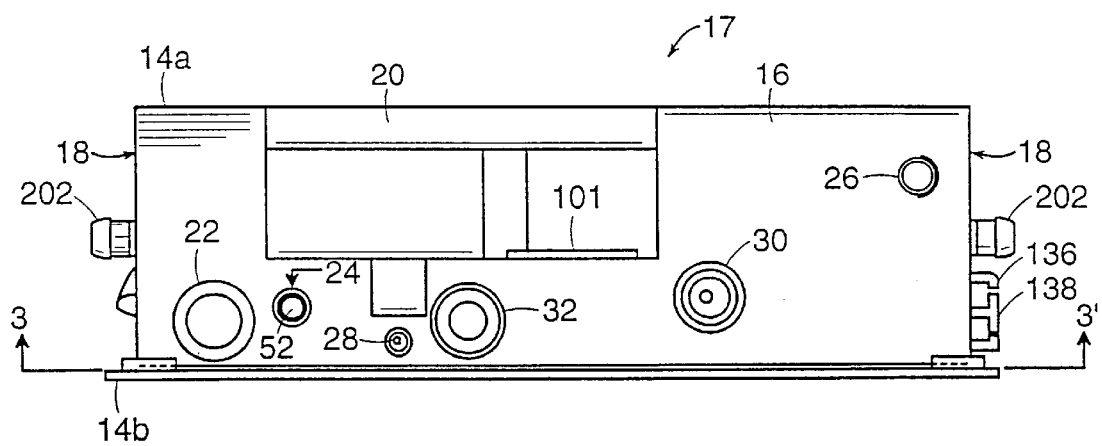
FIG. 2 is a top view of the device of FIG. 1.
Figure 9:
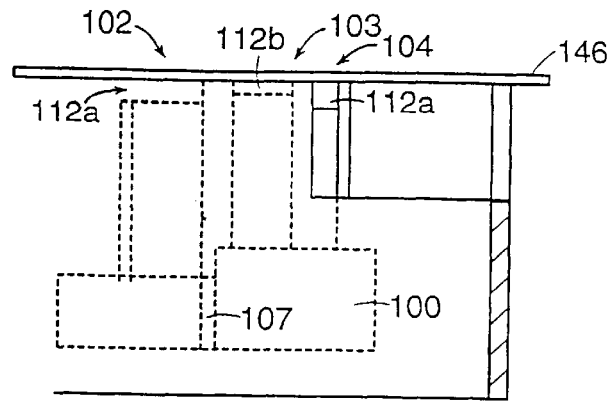
FIG. 9 is an elevation view taken along line 9–9' of FIG. 3 with the front panel on the body portion.
Figure 10:
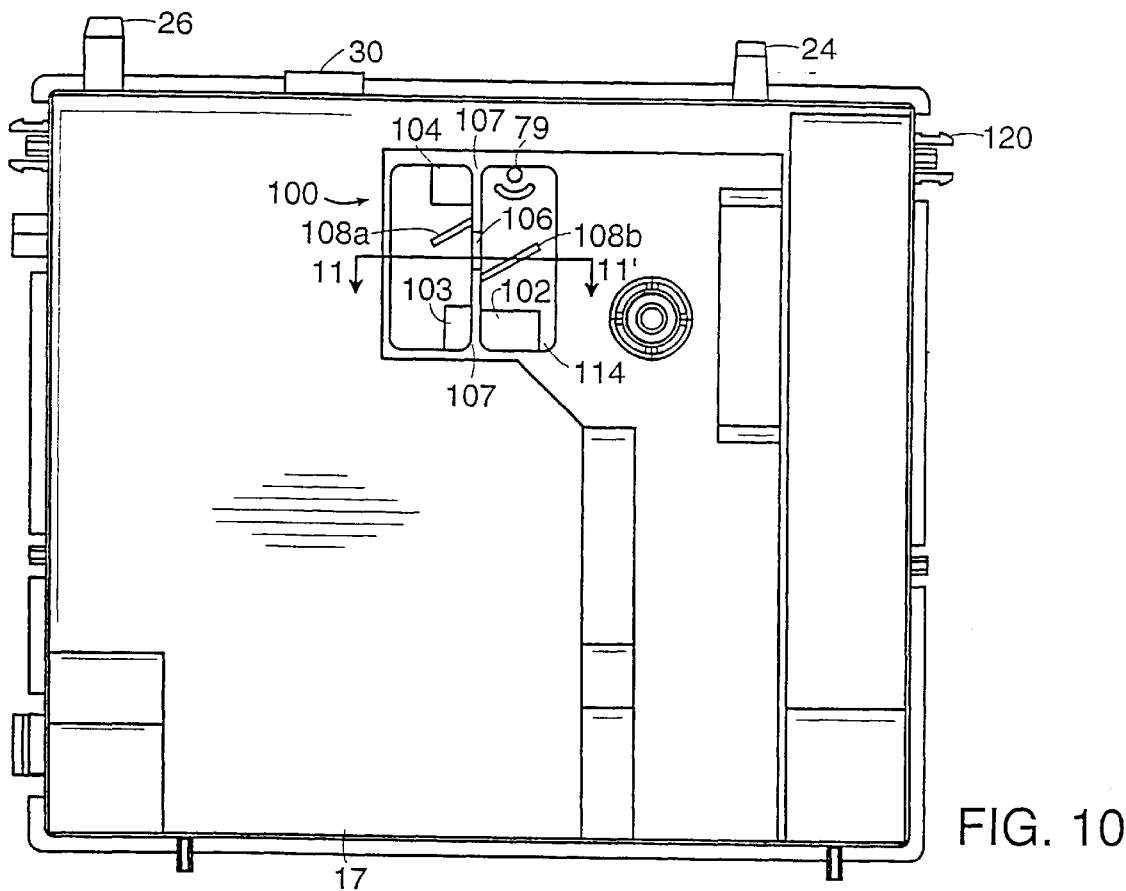
FIG. 10 is an elevation view of the back of the device with the cover over the intermediate chamber removed.
Figure 11:
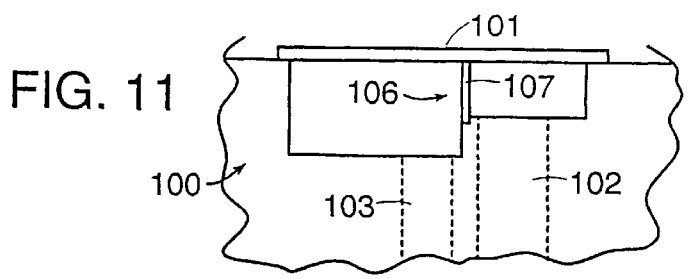
FIG. 11 is a cross-sectional elevation view of the intermediate chamber, with the cover, on taken along section line 11–11' of FIG. 10 with the angled members excluded for clarity.

Referring now to FIGS. 2–3 and FIGS. 9–11, the drainage device 10 preferably includes a novel vent path arrangement that fluidly couples the air leak meter chamber 48 and correspondingly the suction pressure regulation chamber 46 to the collection chamber 50. Preferably, the vent path arrangement includes an intermediate chamber 100 and three passages 102,103,104 fluidly coupled thereto. As shown in FIG. 2 and FIG. 11, the intermediate chamber 100 is sealed with a cover member 101 to prevent the influx of air into the collection chamber 50. The cover member 101 preferably is constructed of the same materials as is the body portion 14a.

One passage, the first passage 102 fluidly couples the air leak meter chamber 48 with the intermediate chamber 100 and the second and third passages 103,104 fluidly couple the intermediate chamber and the collection chamber 50. These three passages 102,103,104 are arranged essentially perpendicular to the surface of the front panel 14b so the passages extend in a front to back relationship.

Preferably, the body portion 14a is molded so the ports, the walls, ribs and partitions, internal to the body portion, the first, second and third passages 102,103,104, the intermediate chamber 100, including the stepped opening 106, the angled members 108a,108b and interior partitions 107 are all formed at the same time. This minimizes assembly time and also reduces the possibility of leakage that would be present if the intermediate chamber 100 was a separate part secured to the device housing 12. However, it is within the scope of the instant invention for the housing 12 to be constructed using any of a number of techniques known to those skilled in the art.

As shown in FIG. 3 and FIG. 9, the three passages 102,103,104 are generally rectilinear in cross section, where three sides of each passage extend and are sealed to the front panel 14b. The fourth side 110a,110b,110c, respectively of the first, second and third passages 102,103,104 are stepped walls spaced from the front panel 14b, so as to form a through opening 112a,112b,112c for each passage. The openings 112b, 112c in the second and third passages 103,104 create a flow path for the gases flowing out of the collection chamber 50 to the suction source via the intermediate chamber 100. The primary vent pathway from the collection chamber 50 is the third passage 104 and the secondary vent pathway is the second passage 103.

During normal operating conditions, the level of fluid in the collection chamber 50 lies well below the openings 112b,112c in the second and third passages 103,104. However, if the drainage device 10 is inadvertently knocked onto its back surface 17, then the level of the liquid in the collection chamber will re-adjust. As such, the fourth sides 110b,110c of the second and third passages 103,104 also are spaced a preset distance from the front panel 14b so the level of the liquid in the collection chamber 50 should lie below the openings 112b,112c when the device is on its back surface. This minimizes the potential for cross contamination of the air leak meter chamber 48 as well as other parts of the device 10 with liquid from the collection chamber 50. This also allows the drainage device to continue to operate or function without interruption.

If the drainage device 10 is inadvertently knocked onto the front panel 14b, the liquid level in the collection chamber also will re-adjust but the openings 112b,112c in the second and third passages 103,104 could be submerged below the liquid level. As such, a liquid level will rise within the second and third passages 103,104 as the level re-adjusts within the collection chamber 50. The fluid level within the second and third passages 103,104 will continue to rise until the liquid from the passages spills over into the intermediate chamber 100 or until the level becomes stabilized in the collection chamber So. As illustrated in FIGS. 10–11, the intermediate chamber 100 includes a stepped opening 106 so an overflow condition does not immediately result in cross-contamination or cross communication with the first passage 102 and the chamber 48 fluidly connected thereto.

In a preferred embodiment, the length of the second and third passages 103,104 and the height of the step in the intermediate chamber stepped opening 106 are selected so the amount of fluid typically accumulated in a drainage device 10, before it is replaced, does not create a fluid level in the collection chamber which will result in a cross contamination. This also allows a handle 13 and the required access for a hand to be formed directly into the body portion 14a so the handle does not project above the top 16. However, it is within the scope of the instant invention for the length of the second and third passages 103,104 and/or the height of the step to be increased or decreased to handle any desired quantity of liquid, including the maximum volume content of the collection chamber 50.

Although FIGS. 9–11 illustrate the two flat surfaces on either side of the partitions 107 as being spaced differently from the cover member 101, this is not a limitation. In an alternate embodiment, the two flat surfaces are equally spaced from the cover member 101 and a stepped wall or partition is provided to establish the intermediate chamber stepped opening 106, e.g., see the stepped partition 114 in the collection chamber 50. It is also within the scope of the instant invention for the two flat surface to be equally spaced from the cover member 101 and there be no stepped opening therebetween, but rather just an opening. In this case, the lengths of the second passage 103 and the third passage 104 are selected so the liquid rising in these passages when the device 10 is on its front panel 14b does not spill over into the intermediate chamber 100.

When the drainage device 10 is uprighted, any liquid in the third passage 104, flows into the intermediate chamber 100 and then this fluid, any fluid in the intermediate chamber and any fluid in the second passage 103 flows back into the collection chamber 50 via the second passage. The spatial separation of the second and third passages 103,104 prevents syphoning of the fluid in the passages and/or intermediate chamber 100 into the air leak meter chamber 48 after the device is uprighted.

The intermediate chamber also includes two angled members 108a,108b that direct the fluid flowing in the intermediate chamber 100 to the second passage 103 and away from the first passage 102. For example, one of the angled members, member 108a, is angled so the fluid exiting the third passage 104, impinges on the angled member and is directed outwardly away from the first passage 102.

As indicated above, three sides of the first passage 102 extend and are sealed to the front panel 14b and the fourth side 110a is spaced therefrom to create an opening 112a or flow path for the gases passing through the collection chamber 50. The first passage fourth side 110a also is spaced from the front panel so the fluid, if any, in the air leak meter chamber 48 is not communicated to the collection chamber 50 if the drainage device 10 inadvertently falls on its back surface 17. In addition, the small arm 99 of the air leakage chamber 48 is configured so as to retain the fluid volume therein. As with the second and third passages 103,104, the opening 112a formed in the end of the first passage 102 could be submerged below the fluid level if the device 10 falls onto its' face panel 14b. However, the volume of the small arm 99 in conjunction with the volume of the first passage 102 is established so the fluid volume used for leak detection and monitoring does not spill over and mix with the fluids in the collection chamber 50.

It is possible that a patient or user may create a high negativity pressure condition within the collection chamber 50, which in turn syphons the fluid out of the cavity 86 in the air leak meter chamber 48 and upwardly in the small arm 99 thereof. One of the partitions 107 defining the stepped opening 106 in the intermediate chamber 100 and one angled member 108b establish a compartment 109 in the intermediate chamber that can receive the fluid from the air leak meter chamber 48. The fluid is retained in this compartment 109 and is not communicated via the intermediate chamber 100 and the second passage 103 to the collection chamber 50. When the high negativity condition is removed, e.g., by a user actuating the manual high negative pressure valve 30, the fluid is returned by gravity to the air leak meter chamber 48.

The large arm 95 of the air leak meter chamber 48 also includes a stepped wall member 87 that extends between two side walls so as to form a barrier. This barrier is provided principally to prevent fluid or bubbling fluid from contacting the one-way valve 84 and the automatic high negativity relief valve 34 but still provide a flow path for gases.

The collection chamber 50 includes two partitions 114, 115 that define three compartments 116a–c. The first compartment 116a communicates with the drain line port 26 and receives the gas and liquid discharges from the drain line 6. Each partition 114,115 includes an aperture 118 so the gaseous discharges are communicated via the first, second and third passages 102,103,104 to the suction source. Each aperture 118 also provides a mechanism for directing the liquids onto the next compartment after the upstream compartment has become filled. Each aperture 118 also is stepped or spaced a preset distance from the front panel 14b as a mechanism for limiting the flow of liquids between compartments 116a,116b,116c when the drainage device 10 is on its back surface 17.

As indicated above, a window 44a,44b,44c is provided for each of the compartments 116a,116b,116c so a user can readily determine the amount of fluid which has been accumulated in a given compartment as well as in the collection chamber 50. Such information can be used to determine the presence of, for example a post operative problem or condition. The housing 12 also can be configured with resealable grommets, e.g. like the grommet 32 for introducing the fluid into the air leak meter chamber 48, that communicate with the compartments 116a,116b,116c. This permits a user to insert a needle into any one of the compartments for the purposes of obtaining a sample of the fluid being accumulated for analysis.

As shown in FIG. 2 and FIGS. 4A–C a hanger attachment 120 or mounting is provided on each side 18 of the housing 12 to which is rotatably secured a hanger 200 as shown in FIGS. 12A–G. Each hanger attachment 120 includes two flexible arcuate arms 122 about a common axis that each subscribe a portion of a circumference. Also included is a center portion 124 that provides an area of radial support for the hanger for a portion of the circumference not subtended by the flexible arms. As more clearly seen in FIG. 4C, the front edge of the center portion 124 is disposed behind the front edge of the flexible arms 122. This allows the flexible arms 122 to deflect inwardly towards the common axis about the point of attachment to the housing 12 and so the hub 202 of the hanger 200 can be rotatably secured thereon.

Each flexible arm 122 includes a sloping nose 126 and a recess 128. In use, the hanger hub 202 is pushed axially against the sloping nose 126 so the raised region 206 in the aperture 208 in the hub 202 contacts the sloping nose. The sliding engagement of the hub raised region 206 and the sloping nose 126 as the hub is moved axially causes each flexible arm 122 to deflect. When the hub's raised region 206 moves into the recess 128 of a flexible arm 122, the flexible arm snaps back and the leading edge of the recess engages the hub's raised region 206, thereby securing the hanger 200 to the hanger attachment 120. Such an arrangement permits a single style of hanger 200 to be mounted to the hanger attachment 120 on either the left or right side of the device housing 12.

The hanger attachment center portion 124 preferably includes a sloping nose 130 and a recess 132 to engage detents provided on axially extending legs of a cap. In use the axially extending legs are inserted in the area 134 between the flexible arms 122 and the center portion 124 until the cap leg detents engage the leading edge of the center portion recess 132. The cap has a generally circular shape and is dimensioned to cover at least the exposed region interior to the hanger hub 202. More particularly, the cap outer diameter corresponds to the outer diameter of the hanger hub 202.

As shown in FIGS. 12A–G, each hanger 200 of the instant invention is configured with an attachment member 204 that extends from the hub 202 and can be used to attach or hang the device 10 from a support structure such as the side rail of a hospital bed, an I.V. pole, a wheel chair or the side rails of a gurney. The hanger attachment member 204 is formed as an integral structure with an angled region 210; a straight region 212 and a hook region 214, where the angled region 210 interconnects the hanger attachment member 204 and the hub 202. Preferably, the hanger attachment member 204 is formed along with the hub 202, from plastic material such as ABS, so the hanger 200 is an integral structure.

In an exemplary embodiment, the straight and hook regions 212,214 are formed with raised members 216 or webs extending outwardly from the faces 218 of each side, as illustrated in FIG. 12C, to form an I-beam like structure. The ends 220 of the raised members 216, also preferably are interconnected by an arcuate section that traverses each face 218. It should be recognized that any of a number of techniques or structures may be used to yield an attachment member 204 having the desired rigidity and shape for the intended use.

In use, it is typically necessary to bend the hanger attachment member 204 to conform to the available space on the support structure. As such, the angled region 210 preferably includes a flex point 222 about which the hanger attachment member 204 can be reasonably bent without structural failure. Also, the hanger attachment member 204 can be bent about the flex point 222 without snapping the hanger 200 off the housing attachment 120.

In the illustrated embodiment, the flex point 222 is established by stopping the raised members 216 on both faces 218 in the same area in the angled region 110. The spacing of the raised members 216 to create a flex point 222 is dependent upon a number of factors such as the thickness and width and materials used for the base member (i.e. member without raised region), the forces that can be applied during the intended use and manufacturing limitations. In a particular embodiment, the flex point 222 was established by providing a straight length of about 0.250 in. along the edge of a ⅛ in. by 5/16 in. plastic member without the raised members 216 (i.e., surface is flat). In addition, the arcuate region portions of the raised members traversing the faces 218 were spaced apart by about 0.125 in.

In some cases, the liquid being drained from a body cavity is essentially the patient's blood that may include some products, such as bone fragments or clots that can be easily filtered out. Given today's concern with diseases communicable by blood transfusion as well as the rareness of some blood types, it is advantageous to be able to drain, collect and reinfuse a patient with their own blood (i.e., autotransfusion).

Figure 13A:
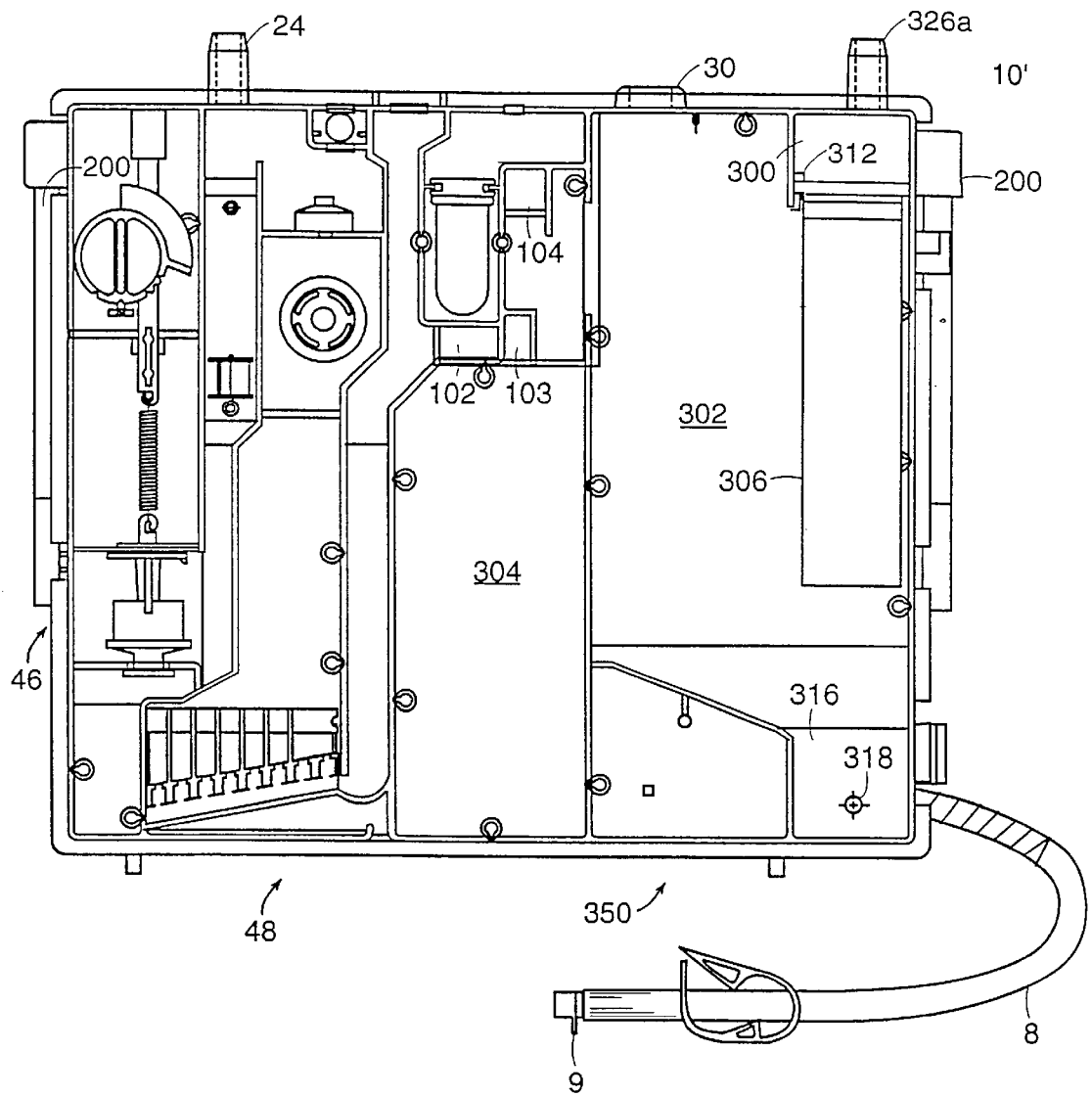
FIG. 13A is a cross sectional front view of an alternative drainage device embodiment.
Figure 13B:
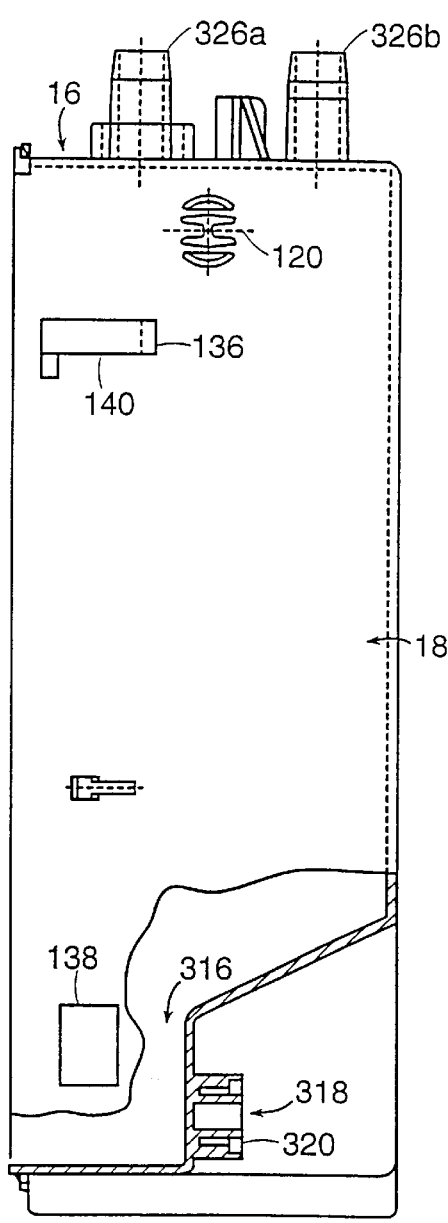
FIG. 13B is a side view with a partial breakaway and cross sectional view of the drainage device of FIG. 13A.
Figure 13C:
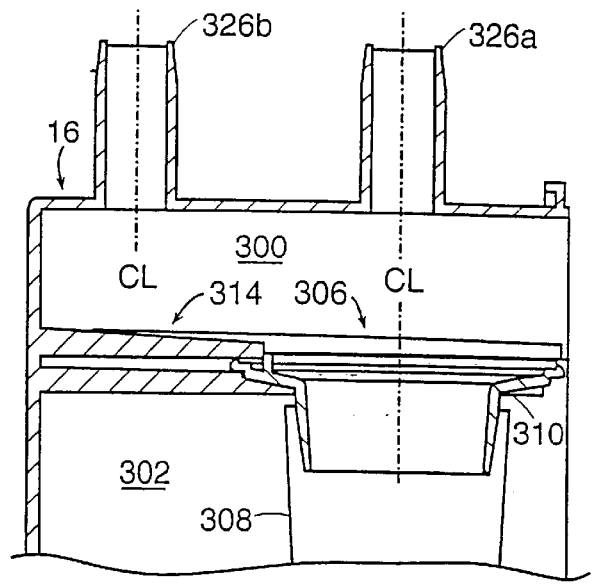
FIG. 13C is a partial cross-sectional elevation view of the device of FIG. 13B taken through the patient drain ports.

There is shown in FIG. 13A a cross sectional front view of an alternate drainage device 10' that can continuously collect and filter blood from a body cavity and provide a continuous output to a device or apparatus such as an I.V. infusion pump (not shown) to reinfuse the patient with their own blood. The foregoing figures and discussion for the pressure regulation chamber 46, the air leak meter chamber 48 and the improved vent path arrangement as well as other features of the above described drainage device 10, apply equally to the corresponding features of the alternate drainage device embodiment 10'. As such, they are not specifically discussed further herein.

Figure 13D:
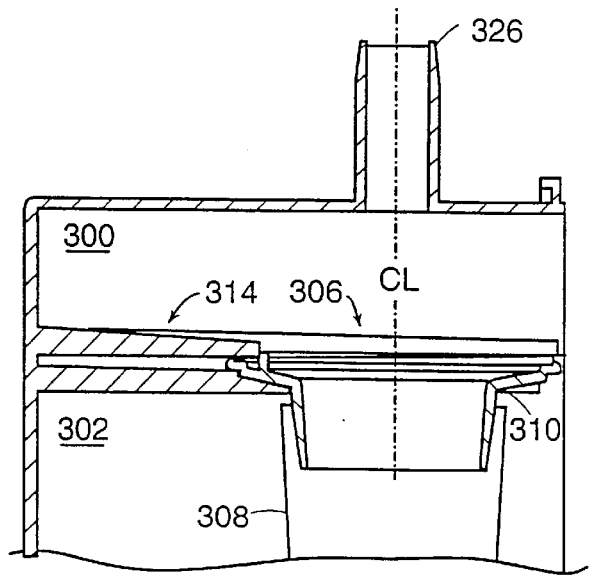
FIG. 13D is a partial cross-sectional elevation view of an alternative embodiment of the device of FIG. 13.

As shown in FIG. 13A, the wall and partitions internal to the device housing 12' are arranged so the collection chamber 350 includes three compartments 300, 302, 304 and a filtering element 306. The first compartment is fluidly coupled to the two patient drain line ports 326a, 326b to receive the blood to be filtered. It is not uncommon to see a patient with two or more post-operative chest drain lines. As such, in the instant embodiment the device 10' includes two drain ports 326a, 326b so a single device can be used for multiple drain line applications. Alternatively, a device 10' can be configured with a single drain port 326 as is shown in FIG. 13D.

The first compartment 300 also is configured so the blood flows into the second compartment via a filter element 306. In an exemplary embodiment, the filter element 306 includes a 200 micron mesh filter sock 308 that is ultrasonically welded to a filter shelf 310. The filter sock 308 can be any number of mesh sizes that can filter out bone fragments, blood clots, tissue and the like while allowing gases and red blood cells to flow unimpeded therethrough. Although a filter sock 308 is illustrated, the filter element can be any of a number of filtering means known to those skilled in the art such as a flat filter medium.

The filter shelf 310 is slid in two side brackets 312 until it contacts and engages a rear shelf bracket 314. The rear shelf bracket 314, preferably is sloped frontwardly so as to direct any blood from the second drain line port 326b to the filter sock 308. The engagement of the filter shelf 310 with the side brackets 312, the rear bracket 314 and the front panel 14b establish the first compartment 300.

The second compartment 302 is designed with sloping surfaces, in the bottom of the compartment so as to create a sump 316 that is in fluid communication with an output port 318. The sloping surfaces, as seen in FIGS. 13A,B, are generally sloped side to side and front to back so as to direct the blood towards the output port 318. The sump 316 is generally configured to assure that the output port 318 is submerged while supplying blood in the output line 8 for re-infusion. The re-infusion line 8 is a PVC tube that is slipped into the annular ring 320 in the output port 306. The re-infusion line 8 also preferably includes a spike port 9 to facilitate connecting the line 8 to the distribution device.

The third compartment 304 essentially corresponds to the third compartment 116c described above and shown in FIG. 3. In the instant embodiment, the third compartment 304 is configured to handle overflows that may occur because of a blockage in the output lines or other situations that might develop where blood is not being re-infused at the same rate as it is being collected. Although the illustrated embodiment shows the third compartment 304 as not being fluidly coupled to the second compartment 302, it also is within the scope of the instant invention for the second and third compartments 302,304 to be configured so 20 they are fluidly coupled.

In operation, a user connects the drain line ports 326a,b to the appropriate drain lines 6 from a body cavity and establishes suction pressure conditions in the collection chamber 350. After a sufficient quantity of filtered blood is accumulated in the collection chamber 350, the user begins to re-infuse the patient's collected blood into the patient. The autotransfusion process of collection, filtering and re-infusion continues automatically until the user terminates the process. While this process is ongoing, the fluid levels in the second compartment 302 are periodically checked, e.g., by means of the indicia marked window, to determine if there is sufficient blood in the first compartment to continue autotransfusion or whether to terminate the process. However, there are various other reasons which can lead to termination of the process.

Figure 14A:
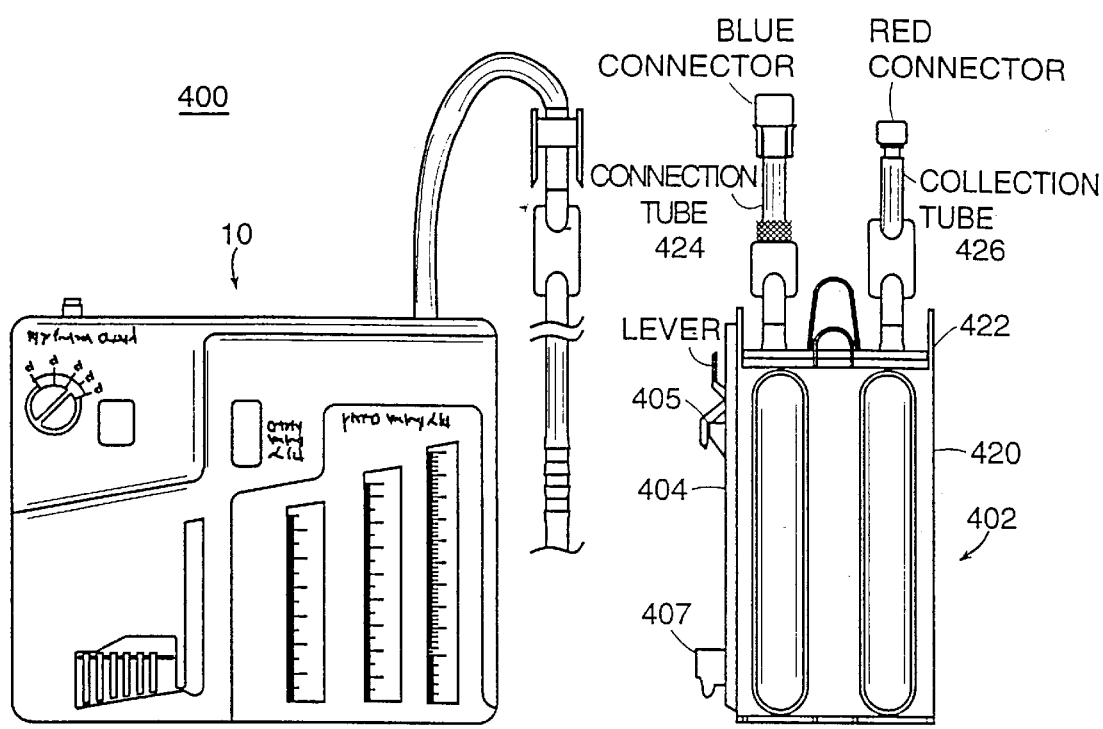
FIGS. 14A, B are schematic views respectively of an autotransfusion drainage system according to the instant invention.
Figure 14B:
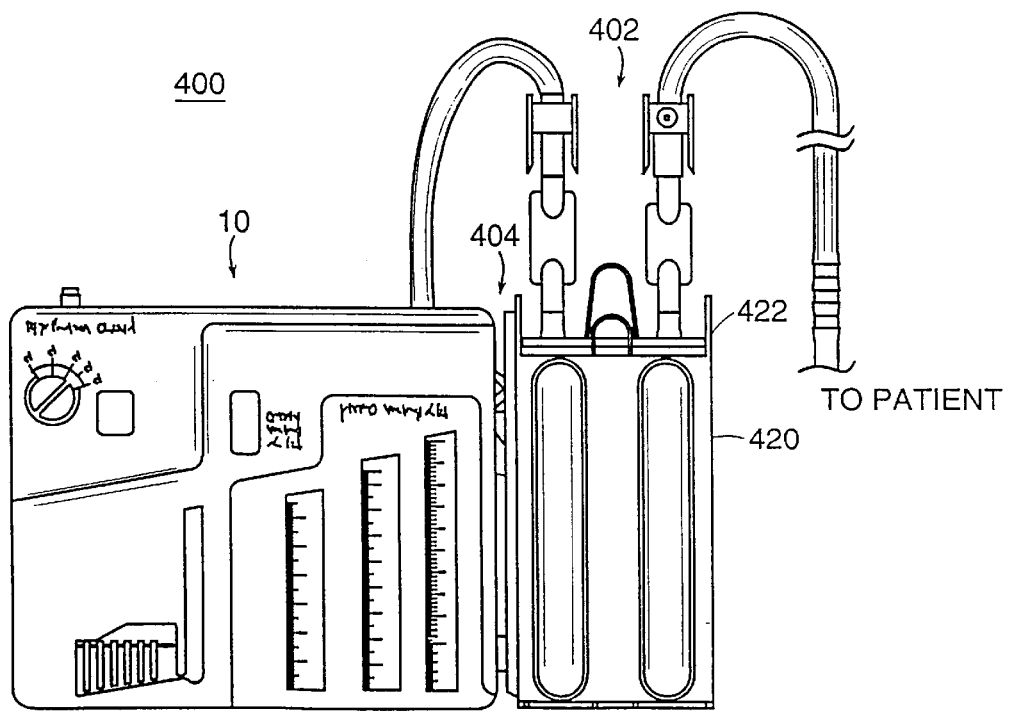

Alternatively, a system 400 including the drainage device 10, an external autotransfusion bag assembly 402, and an interface member 404 can be used for purposes of collecting and re-infusing a patient's blood back into the patient. In this process, the blood can be filtered along with collecting the blood, when re-infusing the blood or a combination of the two. Schematic views of such an autotransfusion system in an unassembled and assembled condition are shown in FIGS. 14A,B, respectively. Various views of the interface member 404, also are shown in FIGS. 15A–E.

The autotransfusion bag assembly 402 includes a plastic bag 420 disposed in a support frame 422, e.g., a metal wire type of frame. The plastic bag 420 includes a connection tube 424 and collection tube 426. The bag also includes a spike port, as is known in the art, for purposes of re-infusing the collected blood. The connection tube 424 is fluidly connected to the drain line port 26 of the drainage device 10 and the collection tube 426 is coupled to the drain line from the body cavity of the patient. Thus when a negative pressure or suction condition is established in the collection chamber 50, gas and the liquid, i.e. blood, is drawn into the plastic bag 420. The blood remains in the plastic bag 420 and the gas, if any, passes through the connection tube 424 and any interconnecting tubing to the collection chamber 50. Thereafter, the gas is drawn through the device 10 as hereinabove described.

The autotransfusion bag assembly 402 is mounted to the drainage device 10 by means of an interface member 404. The interface member 404 removably engages the support frame 422 of the bag assembly 402 using any of a number methods known to those skilled in the art. In an exemplary embodiment, the interface member 404 includes a plate member 412 at one end that slides behind a horizontal member of the support frame 422 and a clip member 414 proximate the other end that clips onto another horizontal 414 member of the support frame.

The interface member 404 also includes a lever actuated member 405 at one end thereof for removably engaging the horizontal support member 136 (see FIGS. 2,3,4A) that is provided on one side 18 of the device housing 12. The lever actuate member 405 member includes a detent 406 at one end for engaging the bottom surface 140 of the support member 136.

Figure 4A:
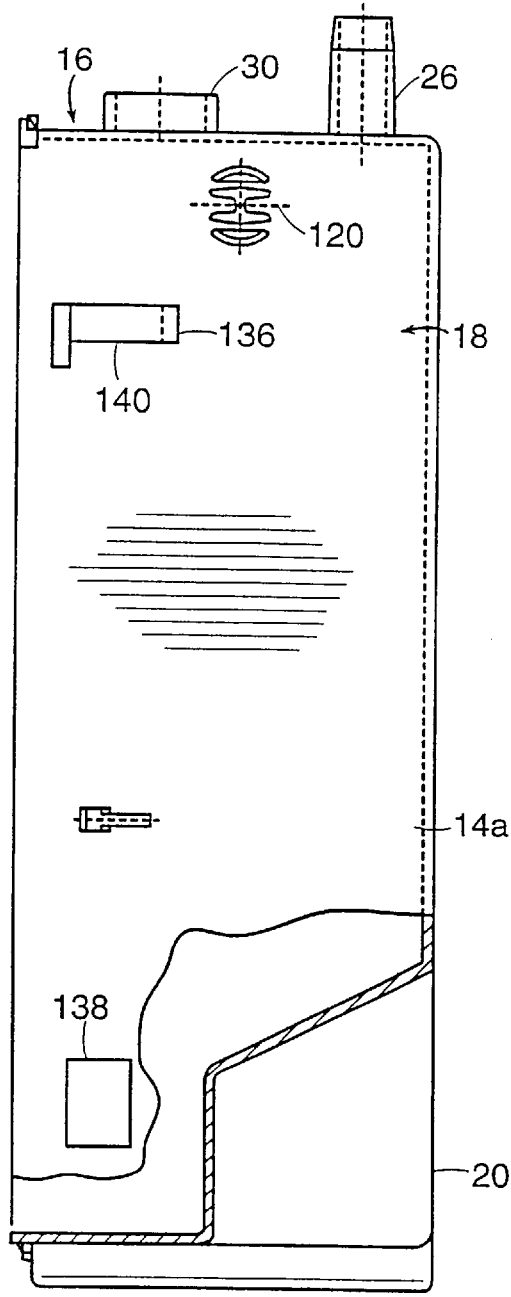
FIG. 4A is a side view of the device of FIG. 1 with the hangers removed.
Figure 4B:
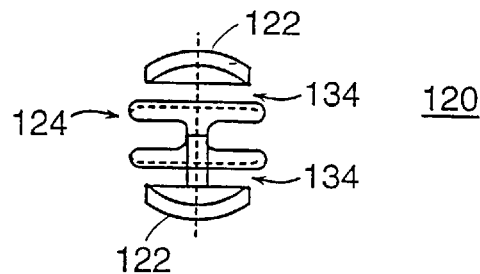
FIG. 4B is a front enlarged view of the device hanger attachment of FIG. 4A.
Figure 4C:
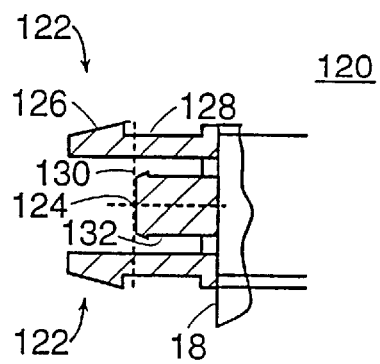
FIG. 4C is a cross-sectional side view of the device hanger attachment of FIG. 4B.
Figure 5A:
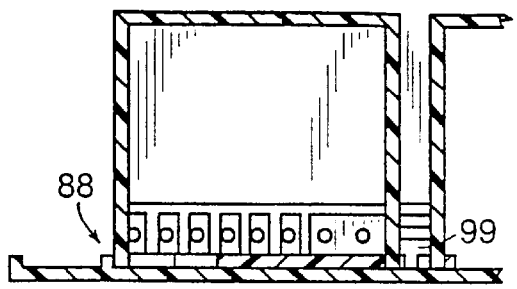
FIG. 5A is section 5–5' of FIG. 3.
Figure 5D:
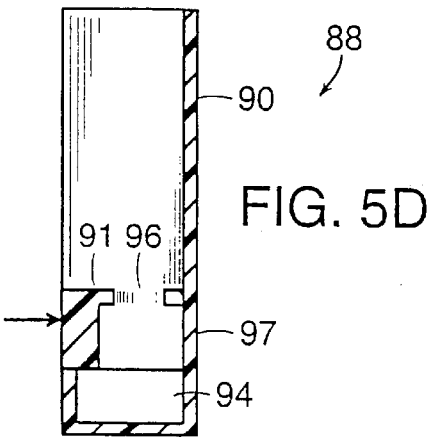
FIGS. 5B–D are various views of the air flow meter.
Figure 5B:
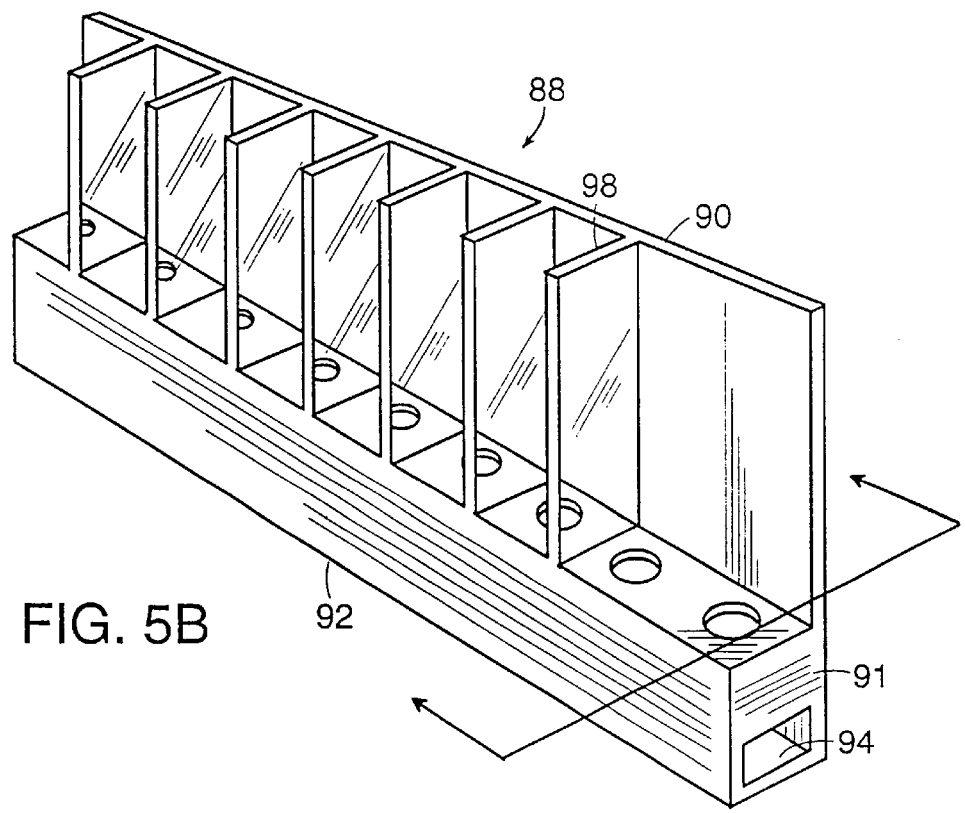
Figure 5C:
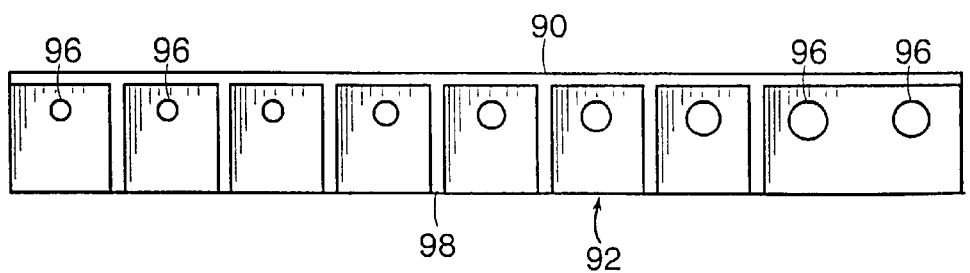

A fixed member 407 is secured to the other end of the interface member for slidably engaging the lower support member 138 on the device housing. As shown in FIGS. 2,4A, the lower support member 138 is a T-shaped projection from the side 18 of the device housing 12. The fixed member 407 is configured so as to removably and slidably receive this shaped member.

In an exemplary embodiment, the fixed member 407 includes downwardly extending finger portions 408 that are spaced from each other so the fixed portion can be centered on the vertical portion of the T-shaped support member 138. As the interface member 404 is slid downward, the flat/horizontal portion of the T-shaped support member 138 is received in a pocket 409 in the fixed member 407 and is retained in the pocket by a member 410 that projects over at least a portion of the pocket. This projecting 410 member may also include a notch to receive the vertical portion of the T-shaped support member.

In use, a user releasably secures the autotransfusion bag assembly 400 to the interface member 404. The fixed member 407 and lever actuated member 405 are positioned so they can be slidably received by the corresponding support member 136,138 of the drainage device housing 12. The bag assembly 400 is moved downwardly with respect to the device housing until the detent 406 of the lever actuated member 405 engages the lower surface 140.

The user then interconnects the connection and collection tubes 424,426 to the drain line 6 from the body cavity and the drain line port 26 of the device 10 respectively. Suction or negative pressure conditions are established within the drainage device 10 whereby the blood and any gases are drawn from the body cavity and the blood is collected in the plastic bag 420. This continues until the external bag is filled or is otherwise needed for re-infusion of blood.

Thereafter, a user stops the drainage device 10 and reduces the negativity in the collection chamber 50 using the high negativity relief valve 30. The connection and collection tubing 424,426 is disconnected from the body cavity drain line and the drainage device 10. The user presses on the lever portion of the lever actuated member 405 so it can be disconnected from the corresponding mating receptacle 136 and the user lifts the bag assembly 400 upwardly to free it from the drainage device 10.

The plastic bag 420 is removed from the support frame 422 and prepared for reinfusion by inserting a microaggregate filter into the spike port, attaching an infusion set thereto, evacuating residual air from the bag, priming the filter and drip chamber and suspending the bag from an I.V. pole. If the user wants to continue collecting blood from the patient's body cavity, then a fresh autotransfusion bag assembly 400 is attached and connected to the drainage device 10 as well as being connected to the patient's body cavity. The drainage device 10 re-establishes suction conditions and the draining process is re-started.

Although the features of the instant invention are described herein in combination with a device having a waterless pressure regulator and waterless seal, this is not a limitation as to the application or use of the features in other devices known to those skilled in the art. As such, it is within the scope of the instant invention for the above-described novel vent path arrangement to be used in combination with a device where suction control and/or the patient seal is established using any of a number of techniques including those using manometers. Similarly, the above-described negative pressure indicator and hanger system can be used with other devices.

Although a preferred embodiment of the invention has been described using specific terms, such description is for illustrative purposes only, and it is to be understood that changes and variations may be made without departing from the spirit or scope of the following claims.

What is claimed is:

1. A drainage device comprising:

a housing having front and back surfaces;

at least two chambers in said housing and including a pressure regulation chamber and a collection chamber therein and said pressure regulation chamber and said collection chamber are fluidly coupled by means of a vent pathway;

wherein the vent pathway includes an intermediate chamber and at least first and second passages, each passage being in fluid communication with the interior of the intermediate chamber;

wherein an opening is provided in the first passage, distal from the intermediate chamber, to fluidly couple the first passage and the pressure regulation chamber;

wherein an opening is provided in the second passage, distal from the intermediate chamber, to fluidly couple the second passage and the collection chamber; and a negative pressure indicator associated with the collection chamber to provide a visual indication of the existence of negative pressure within the collection chamber through the front surface of the housing and a suction pressure indicator associated with the pressure regulation chamber to indicate the existence of suction pressure in the pressure regulation chamber.

2. The drainage device of claim 1 further comprising a third passage being spaced from the first and second passages and communicating with the interior of the intermediate chamber and wherein an opening is provided in the third passage, distal from the intermediate chamber, to fluidly couple the third passage and the collection chamber and the suction pressure indicator is associated with the pressure regulation chamber to provide a visual indication of the existence of suction pressure in the pressure regulation chamber through the front surface of the housing.

3. The drainage device of claim 1 wherein the pressure regulation chamber is fluidly interconnected to a port to atmosphere and a suction line port being interconnected to a suction source and wherein the drainage device further comprises:

a suction pressure regulator valve that selectively controls the suction pressure, being developed within the pressure regulation chamber and being applied to the collection chamber, to selected suction pressure levels;

wherein the pressure regulation valve includes a mechanism for moving the regulation valve between open and closed positions when the suction pressure of the suction source is different than the selected suction pressure level, thereby isolating the suction line port from the atmospheric port in the closed position, and for opening the valve when the suction pressure of the suction source exceeds the selected suction pressure level, whereby the atmospheric port is fluidly interconnected to the suction line port so as to maintain the suction pressure being applied at about the selected suction pressure level; and wherein the pressure regulation chamber and the collection chamber are in selective fluid communication with each other by a one-way valve disposed therebetween, where in one position the one-way valve isolates the regulation and collection chambers from each other so gas does not flow to the collection chamber and where, in another position, the one-way valve puts the chambers in fluid communication with each other so suction pressure from the pressure regulation chamber is applied to the collection chamber to thereby cause the drainage of fluids from a body cavity.

4. The drainage device of claim 3 further comprising an air leak meter chamber being fluidly coupled to the collection chamber and the one-way valve, the air leak chamber including a flow meter responsive to the gas flow from the collection chamber and providing a visual indication of a relative flow rate of the gas flowing from the collection chamber to the pressure regulation chamber through the front surface of the housing.

5. The drainage device of claim 3 further comprising the negative pressure indicator which is fluidly coupled to the collection chamber so the negative pressure indicator provides a visual indication of the presence of negative pressure conditions within the collection chamber wherein at least a portion of the negative pressure indicator collapses in response to the existence of negative pressure in the collection chamber.

6. The drainage device of claim 3 further including the front surface of the housing having opaque regions thereon and a negative pressure indicator window thereon to allow for the visual observation of the existence of a negative pressure in the collection chamber through the negative pressure indicator window.

7. The drainage device of claim 6, wherein the front surface further includes a suction status window and an air leak window thereon to allow for the visual observation of a suction status indicator and an air leak indicator therethrough.

8. The drainage device of claim 1 wherein the negative pressure indicator includes a message post encased by a flexible membrane and the interior of the flexible membrane is in fluid communication with the collection chamber so the flexible material collapses upon the message post and renders the message thereon visible in response to negative pressure in the collection chamber.

9. The drainage device of claim 1 further including a wall member separating the pressure regulation chamber and the collection chamber to define a pressure boundary therebetween and a one-way valve on said wall member to allow fluid communication therebetween.

10. A drainage device comprising:

at least two chambers, a pressure regulation chamber and a collection chamber, being interconnected by a plurality of walls and fluidly coupled by a vent pathway; and wherein at least one of said plurality of walls includes an opaque region thereon and a negative pressure indicator window thereon to allow for the visual observation of an indication of a negative pressure in the collection chamber through the negative pressure indicator window.

11. The drainage device of claim 10 wherein a negative pressure indicator is associated with the collection chamber to provide a visual indication of the existence of negative pressure within the collection chamber and the negative pressure indicator is visually observable through the negative pressure indicator window located on one of said plurality of walls; and a suction status indicator is associated with the pressure regulation chamber to provide a visual indication of the existence of suction pressure in the pressure regulation chamber and the suction pressure indicator is visually observable through a suction status window located on said one of said plurality of walls.

12. The drainage device of claim 10, wherein said one of said plurality of walls further includes an air leak window thereon to allow for the visual observation of an air leak indicator therethrough.

13. The drainage device of claim 10 further including a wall member separating the pressure regulation chamber and the collection chamber to define a pressure boundary therebetween and a one-way valve on said wall member to allow fluid communication therebetween.

14. The drainage device of claim 10 wherein the pressure regulation chamber is fluidly interconnected to a port to atmosphere and a suction line port that is interconnected to a suction source and wherein the drainage device further comprises a suction pressure regulator valve that selectively controls the suction pressure being developed within the pressure regulation chamber and applied to the collection chamber to selected suction pressure levels.

15. The drainage device of claim 14 wherein the pressure regulation valve includes a mechanism for moving the regulation valve between open and closed positions when the suction pressure of the suction source is different than the selected suction pressure level, thereby isolating the suction line port from the atmospheric port in the closed position, and for opening the valve when the suction pressure of the suction source exceeds the selected suction pressure level, whereby the atmospheric port is fluidly interconnected to the suction line port so as to maintain the suction pressure being applied at a level generally about the selected suction pressure level.

16. The drainage device of claim 10 wherein the negative pressure indicator window includes a message post adjacent thereto and the message post is encased by a flexible membrane, wherein the interior of the flexible membrane is in fluid communication with the collection chamber so the flexible material collapses upon the message post and renders the message thereon visible in response to negative pressure in the collection chamber.

17. A drainage device comprising:

a pressure regulation chamber, an intermediate chamber and a collection chamber, each of said chambers being interconnected by a plurality of walls and fluidly coupled by a vent pathway;

a negative pressure indicator associated with and adjacent to the collection chamber to provide a visual indication of the existence of negative pressure within the collection chamber; and wherein at least one of said plurality of walls includes a sidewall having an opaque region thereon and a negative pressure indicator window thereon to allow for the visual observation of the negative pressure indicator through the negative pressure indicator window.

18. The drainage device of claim 17 further including a wall member separating the pressure regulation chamber and the collection chamber to define a pressure boundary therebetween and a one-way valve on said wall member to allow fluid communication therebetween.

19. The drainage device of claim 17 further including a suction pressure indicator associated with and adjacent to said pressure regulation chamber.

20. The drainage device of claim 19 further including an air leak meter associated with and adjacent to said intermediate chamber.

21. A drainage device comprising:

at least two chambers, a pressure regulation chamber and a collection chamber, and a plurality of ports, wherein a drain line port is in fluid communication with the collection chamber;

a suction pressure regulator valve that selectively controls the suction pressure, being developed within the pressure regulation chamber and being applied to the collection chamber, to a selected suction pressure level;

wherein the pressure regulation chamber includes two compartments that are selectively interconnected to each other by means of the pressure regulation valve, where one of the ports, the atmospheric port, is in fluid communication with one compartment and another one of the ports, the suction line port, is in communication with the other of the regulation chamber compartments and a suction source;

wherein the pressure regulation valve includes a mechanism for biasing the regulation valve in a first direction when the suction pressure of the suction source is less than the selected predetermined suction pressure level and for biasing the valve in a second direction when the suction pressure of the suction source exceeds the selected suction pressure;

wherein the pressure regulation chamber and the collection chamber are in selective communication with each other by means of a one-way valve disposed on a wall member extending therebetween, where in one position the one-way valve isolates the regulation and collection chambers from each other so gas does not flow to the collection chamber and where, in another position, the one-way valve puts the chambers in communication with each other so suction pressure from the pressure regulation chamber is applied to the collection chamber to thereby cause the drainage of fluids from a body cavity; and wherein the pressure regulation chamber includes a suction pressure indicator associated therewith to provide an indication of the existence of suction pressure in the pressure regulation chamber and the collection chamber includes a negative pressure indicator associated therewith to provide an indication of the existence of negative pressure in the collection chamber.

22. The drainage device of claim 21 further comprising an air leak meter chamber being coupled to the collection chamber and the one-way valve, the air leak chamber including a flow meter responsive to the gas flow from the collection chamber and providing an indication of a relative flow rate of the gas flowing from the collection chamber to the pressure regulation chamber.

23. The drainage device of claim 22 wherein the air flow meter includes a downwardly sloped member having a passage therethrough and a plurality of apertures communicating with the passage, wherein the downwardly sloped member cooperates with the apertures so gas from the collection chamber flows through successively lower apertures as the flow rate of the gas from the collection chamber increases.

24. The drainage device of claim 21 wherein the negative pressure indicator includes a message post encased by a flexible membrane, wherein the interior of the flexible membrane is coupled to the collection chamber so the flexible material collapses upon the message post and renders the message thereon visible.

25. The drainage device of claim 21 further comprising a drain port fluidly coupled to the collection chamber to drain fluid from the collection chamber.

26. The drainage device of claim 21 further including a bag assembly in fluid communication with the collection chamber and removably secured thereto to form an autotransfusion system.

27. A drainage device comprising:

a housing having a plurality of surfaces;

a plurality of chambers including a pressure regulation chamber, an intermediate chamber and a collection chamber therein and said pressure regulation chamber and said collection chamber are fluidly coupled by a vent pathway;

a negative pressure indicator associated with the collection chamber to provide a visual indication of the existence of negative pressure within the collection chamber; and a wall member separating the pressure regulation chamber and the collection chamber to define a pressure boundary therebetween and a one-way valve on said wall member to allow fluid communication therebetween and wherein said negative pressure indicator is on the side of the pressure boundary adjacent to the collection chamber.

28. The drainage device of claim 27 further including a suction status indicator associated with the pressure regulation chamber to provide a visual indication of the existence of suction pressure in the pressure regulation chamber and the suction pressure indicator is positioned on the side of the pressure boundary adjacent to the pressure regulation chamber.

29. The drainage device of claim 27 further including an air leak meter associated with the intermediate chamber to provide a visual indication of the existence of air flow in the intermediate chamber and the air leak meter is positioned on the side of the pressure boundary adjacent to the intermediate chamber.

30. A drainage device comprising:

a housing having a plurality of wall surfaces;

a plurality of chambers in said housing and including a suction pressure regulation chamber, an air leak meter chamber and a collection chamber, and a plurality of ports, wherein a drain line port is in fluid communication with the collection chamber and an atmospheric port and suction line port are in fluid communication with the suction pressure regulation chamber;

a suction pressure regulator valve that selectively controls the suction pressure being developed within the suction pressure regulation chamber and being applied to the collection chamber at a selected suction pressure level;

wherein the suction pressure regulator valve includes a manually adjustable mechanism for biasing the suction pressure regulator valve in a first direction when the suction pressure of the suction source is less than the selected suction pressure level and for biasing the suction pressure regulator valve in a second direction when the suction pressure of the suction source exceeds the selected suction pressure;

wherein the suction pressure regulation chamber and the air leak meter chamber are in selective communication with each other by means of a one-way valve disposed on a wall member extending therebetween, where in one position the one-way valve isolates the suction pressure regulation chamber and air leak meter chamber from each other so gas does not flow from the suction pressure regulation chamber to the air leak meter chamber and where, in another position, the one-way valve puts the chambers in communication with each other so suction pressure from the suction pressure regulation chamber is applied to the air leak meter chamber and collection chamber to thereby cause the drainage of fluids from a body cavity; and wherein the suction pressure regulation chamber includes a suction pressure indicator associated therewith to provide an indication of the existence of suction pressure in the suction pressure regulation chamber and the collection chamber includes a negative pressure indicator associated therewith to provide an indication of the existence of negative pressure in the collection chamber.

31. The drainage device of claim 30 further comprising a negative pressure indicator window on a wall of the housing so the negative pressure indicator is visually observable through the wall of the housing in the presence of negative pressure conditions within the collection chamber.

32. The drainage device of claim 30, further comprising a suction status window on a wall of the housing to allow for the visual observation of the suction status indicator therethrough in the presence of suction pressure in the suction pressure regulation chamber.

33. The drainage device of claim 30 wherein the negative pressure indicator is movable between first and second positions and further comprising a negative pressure indicator window on a wall of the housing so the negative pressure indicator is visually observable through the wall of the housing in a second position thereof to indicate the presence of negative pressure conditions within the collection chamber and wherein the negative pressure indicator is not visually observable therethrough in the first position thereof.

34. The drainage device of claim 33 wherein the negative pressure indicator includes a message post encased by a flexible membrane and the interior of the flexible membrane is in fluid communication with the collection chamber so the flexible material collapses upon the message post and renders the message thereon visible in the second position thereof.

35. The drainage device of claim 33 wherein the negative pressure indicator includes a message post encased by a flexible membrane and the interior of the flexible membrane is in fluid communication with the collection chamber so the flexible material is spaced apart from the message post in the first position thereof.

36. The drainage device of claim 30 wherein the suction status indicator is movable between first and second positions and further including a suction status indicator window on a wall of the housing so the suction status indicator is visually observable through the wall of the housing in a second position thereof to indicate the presence of suction conditions within the suction pressure regulation chamber.

37. The drainage device of claim 30, wherein said one of said plurality of walls further includes an air leak window thereon to allow for the visual observation of at least a portion of the air leak chamber therethrough and the air leak chamber further includes a flow meter that is visually observable through the air leak window.

38. The drainage device of claim 37 wherein the flow meter includes a downwardly sloped member having a passage therethrough and a plurality of apertures communicating with the passage, wherein the downwardly sloped member cooperates with the apertures so gas from the collection chamber flows through successively lower apertures as the flow rate of the gas from the collection chamber increases.

39. A drainage device comprising:

a housing having a plurality of wall surfaces;

a plurality of chambers in said housing and including at least two chambers, a pressure regulation chamber and a collection chamber, being interconnected by a vent pathway fluidly extending therebetween;

a suction status indicator associated with the pressure regulation chamber to provide an indication of the existence of suction pressure in the pressure regulation chamber and the suction status indicator is movable between first and second positions in response to the existence of suction pressure in the pressure regulation chamber;

a negative pressure indicator associated with the collection chamber and the negative pressure indicator is movable between first and second positions in response to the existence of negative pressure in the collection chamber;

wherein at least one of said plurality of walls on said housing includes an opaque region thereon;

a suction status indicator window on said at least one of said plurality of walls to allow for the visual observation of the suction status indicator in the collection chamber through the suction status indicator window when the suction status indicator is in the second position to provide an indication of the existence of suction pressure in the pressure regulation chamber; and a negative pressure indicator window on said at least one of said plurality of walls to allow for the visual observation of the negative pressure indicator in the collection chamber through the negative pressure indicator window when the negative pressure indicator is in the second position to provide an indication of the existence of negative pressure in the collection chamber.

40. The drainage device of claim 39 wherein the negative pressure indicator includes a message post encased by a flexible membrane and the interior of the flexible membrane is in fluid communication with the collection chamber so the flexible material collapses upon the message post and renders the message thereon visible in the second position thereof.

41. The drainage device of claim 39 wherein the suction status indicator includes a message post encased by a flexible membrane and the interior of the flexible membrane is in fluid communication with the pressure regulation chamber so the flexible material collapses upon the message post and renders the message thereon visible in the second position thereof.

42. The drainage device of claim 39 further including an air leak meter chamber disposed between the pressure regulation chamber and the collection chamber and wherein said one of said plurality of walls further includes an air leak window thereon to allow for the visual observation of at least a portion of the air leak chamber therethrough.

43. The drainage device of claim 39 wherein the pressure regulation chamber includes a suction pressure regulator valve that selectively controls the suction pressure being developed within the pressure regulation chamber and being applied to the collection chamber to a selected suction pressure level;

wherein the pressure regulation chamber is in fluid communication with an atmospheric port that is in communication with the atmosphere and a suction line port that is in communication with a source of suction; and wherein the suction pressure regulator valve includes a manually adjustable mechanism for biasing the regulator valve in a first direction when the suction pressure of the suction source is less than the selected suction pressure level and for biasing the valve in a second direction when the suction pressure of the suction source exceeds the selected suction pressure level.

\* \* \* \* \*

UNITED STATES PATENT AND TRADEMARK OFFICE
CERTIFICATE OF CORRECTION

PATENT NO. : 6,338,728 B1
DATED : January 15, 2002
INVENTOR(S) : Michael A. Valerio et al.

It is certified that error appears in the above-identified patent and that said Letters Patent is hereby corrected as shown below:

<u>Column 14,</u>
Line 25, replace "collection chamber So" with -- collection chamber 50 --;

<u>Column 18,</u>
Line 33, replace "compartments 302,304 to be configured so 20 they are" with -- compartments 302,304 to be configured so they are --.

Signed and Sealed this

Fifteenth Day of October, 2002

*Attest:*

*Attesting Officer*

JAMES E. ROGAN
*Director of the United States Patent and Trademark Office*